(12) United States Patent
Walters et al.

(10) Patent No.: US 7,896,917 B2
(45) Date of Patent: *Mar. 1, 2011

(54) METHOD AND APPARATUS FOR GRAFT FIXATION

(75) Inventors: Troy M Walters, Plymouth, IN (US);
Kevin T Stone, Winona Lake, IN (US);
Jason D Meridew, Syracuse, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1509 days.

This patent is subject to a terminal disclaimer.

(21) Appl. No.: 11/201,491

(22) Filed: Aug. 11, 2005

(65) Prior Publication Data
US 2005/0273003 A1 Dec. 8, 2005

Related U.S. Application Data

(63) Continuation-in-part of application No. 10/686,236, filed on Oct. 15, 2003, now Pat. No. 7,341,592.

(51) Int. Cl.
*A61F 2/08* (2006.01)
(52) U.S. Cl. .................................... 623/13.11
(58) Field of Classification Search ............ 606/88, 606/232; 623/13.11–13.2
See application file for complete search history.

(56) References Cited

U.S. PATENT DOCUMENTS

| | | |
|---|---|---|
| 461,621 A | 10/1891 | Rogers |
| 2,695,607 A | 11/1954 | Hipps et al. |
| 3,832,931 A | 9/1974 | Talan et al. |
| 3,871,379 A | 3/1975 | Clarke |
| 4,044,647 A | 8/1977 | Takahashi et al. |
| 4,053,982 A | 10/1977 | Weissman |

(Continued)

FOREIGN PATENT DOCUMENTS

EP 1 360 949 11/2003

(Continued)

OTHER PUBLICATIONS

Allen et al., "Degradation and stabilization of styrene-ethylene-butadiene-styrene (SEBS) block copolymer", Polymer Degradation and Stability, V. 71, p. 113-122. (2001).

*Primary Examiner* — Anu Ramana
(74) *Attorney, Agent, or Firm* — Harness, Dickey

(57) ABSTRACT

An apparatus and method for performing a surgery, especially an ACL replacement surgery, where a flexible strand insertion rod co-operates with a U-Guide apparatus to insert a flexible strand into a tunnel formed in a bone portion and to guide a pair of drill points to form a pair of tunnels transversely to the tunnel of the insertion rod. The drill points are guided through the insertion rod and the flexible strand is held over the drill points as the transverse tunnels are formed. The insertion rod is then removed from the tunnels formed in the bone and the flexible strand is held looped over the second drill point. Subsequently, a soft tissue replacement is affixed to one end of the flexible strand and pulled over up to the first drill point with the other end of the flexible strand. The first drill point is then used to pull a cross pin through the transverse tunnel to hold the looped end of the soft tissue replacement in place. Finally, the two free ends of the soft tissue replacement are affixed to the bone completing the implantation of a soft tissue replacement.

33 Claims, 14 Drawing Sheets

U.S. PATENT DOCUMENTS

| | | | |
|---|---|---|---|
| D249,705 S | 9/1978 | London | |
| 4,257,411 A | 3/1981 | Cho | |
| 4,338,054 A | 7/1982 | Dahl | |
| 4,386,179 A | 5/1983 | Sterling | |
| 4,535,768 A | 8/1985 | Hourahane et al. | |
| 4,537,185 A | 8/1985 | Stednitz | |
| 4,756,307 A | 7/1988 | Crowninshield | |
| 4,922,897 A | 5/1990 | Sapega et al. | |
| 4,932,972 A | 6/1990 | Dunn et al. | |
| 4,950,270 A | 8/1990 | Bowman et al. | |
| 4,985,032 A | 1/1991 | Goble | |
| 4,998,937 A | 3/1991 | Grimes | |
| 5,004,474 A | 4/1991 | Fronk et al. | |
| 5,019,078 A | 5/1991 | Perren et al. | |
| 5,026,374 A | 6/1991 | Dezza et al. | |
| 5,030,219 A | 7/1991 | Matsen, III et al. | |
| 5,041,129 A | 8/1991 | Hayhurst et al. | |
| 5,098,435 A | 3/1992 | Stednitz et al. | |
| 5,100,405 A | 3/1992 | McLaren | |
| 5,100,417 A | 3/1992 | Cerier et al. | |
| 5,108,396 A | 4/1992 | Lackey et al. | |
| 5,112,336 A | 5/1992 | Krevolin et al. | |
| 5,129,902 A | 7/1992 | Goble et al. | |
| 5,139,520 A | 8/1992 | Rosenberg | |
| 5,192,322 A | 3/1993 | Koch et al. | |
| 5,201,744 A | 4/1993 | Jones | |
| 5,234,434 A | 8/1993 | Goble et al. | |
| 5,234,444 A | 8/1993 | Christoudias | |
| 5,257,996 A | 11/1993 | McGuire | |
| 5,258,016 A | 11/1993 | DiPoto et al. | |
| 5,266,075 A | 11/1993 | Clark et al. | |
| 5,300,077 A | 4/1994 | Howell | |
| 5,350,380 A | 9/1994 | Goble et al. | |
| 5,354,300 A | 10/1994 | Goble et al. | |
| 5,356,413 A | 10/1994 | Martins et al. | |
| 5,370,662 A | 12/1994 | Stone et al. | |
| 5,391,029 A | 2/1995 | Fardell | |
| 5,393,302 A | 2/1995 | Clark et al. | |
| 5,397,356 A | 3/1995 | Goble et al. | |
| D357,534 S | 4/1995 | Hayes | |
| 5,423,823 A | 6/1995 | Schmieding | |
| 5,425,733 A | 6/1995 | Schmieding | |
| 5,431,651 A | 7/1995 | Goble | |
| 5,437,677 A | 8/1995 | Shearer et al. | |
| 5,454,365 A | 10/1995 | Bonutti | |
| 5,456,722 A | 10/1995 | McLeod et al. | |
| 5,480,403 A | 1/1996 | Lee et al. | |
| 5,507,812 A | 4/1996 | Moore | |
| 5,540,703 A | 7/1996 | Barker, Jr. et al. | |
| 5,545,180 A | 8/1996 | Le et al. | |
| 5,549,676 A | 8/1996 | Johnson | |
| 5,562,671 A | 10/1996 | Goble et al. | |
| 5,593,408 A | 1/1997 | Gayet et al. | |
| 5,601,562 A | 2/1997 | Wolf et al. | |
| 5,618,314 A | 4/1997 | Harwin et al. | |
| 5,632,748 A | 5/1997 | Beck, Jr. et al. | |
| 5,643,273 A | 7/1997 | Clark | |
| 5,643,320 A | 7/1997 | Lower et al. | |
| 5,665,121 A | 9/1997 | Gie et al. | |
| 5,674,224 A | 10/1997 | Howell et al. | |
| 5,849,013 A | 12/1998 | Whittaker et al. | |
| 5,868,789 A | 2/1999 | Huebner | |
| 5,891,150 A | 4/1999 | Chan | |
| 5,895,425 A | 4/1999 | Grafton et al. | |
| 5,918,604 A | 7/1999 | Whelan | |
| 5,931,839 A | 8/1999 | Medoff | |
| 5,941,885 A | 8/1999 | Jackson | |
| 5,964,764 A | 10/1999 | West, Jr. et al. | |
| 5,980,558 A | 11/1999 | Wiley | |
| 5,984,966 A | 11/1999 | Kiema et al. | |
| 6,039,739 A | 3/2000 | Simon | |
| 6,066,173 A | 5/2000 | McKernan et al. | |
| 6,110,211 A | 8/2000 | Weiss | |
| 6,113,604 A | 9/2000 | Whittaker et al. | |
| 6,132,433 A | 10/2000 | Whelan | |
| 6,146,406 A | 11/2000 | Shluzas et al. | |
| 6,187,742 B1 | 2/2001 | Wozney et al. | |
| 6,231,608 B1 | 5/2001 | Stone | |
| 6,231,611 B1 | 5/2001 | Mosseri | |
| 6,267,766 B1 | 7/2001 | Burkhart | |
| 6,306,138 B1 | 10/2001 | Clark et al. | |
| 6,325,804 B1 | 12/2001 | Wenstrom, Jr. et al. | |
| 6,342,056 B1 | 1/2002 | Mac-Thiong et al. | |
| 6,371,124 B1 | 4/2002 | Whelan | |
| 6,375,684 B1 | 4/2002 | Kriek | |
| 6,379,384 B1 | 4/2002 | McKernan et al. | |
| 6,383,199 B2 | 5/2002 | Carter et al. | |
| 6,436,099 B1 | 8/2002 | Drewry et al. | |
| 6,440,373 B1 | 8/2002 | Gomes et al. | |
| 6,454,768 B1 | 9/2002 | Jackson | |
| 6,494,913 B1 | 12/2002 | Huebner | |
| 6,497,726 B1 | 12/2002 | Carter et al. | |
| 6,499,486 B1 | 12/2002 | Chervitz et al. | |
| 6,511,958 B1 | 1/2003 | Atkinson et al. | |
| 6,514,514 B1 | 2/2003 | Atkinson et al. | |
| 6,517,546 B2 | 2/2003 | Whittaker et al. | |
| 6,517,579 B1 | 2/2003 | Paulos et al. | |
| 6,524,328 B2 | 2/2003 | Levinson | |
| 6,537,319 B2 | 3/2003 | Whelan | |
| 6,540,783 B1 | 4/2003 | Whittaker et al. | |
| 6,562,044 B1 | 5/2003 | Cooper | |
| 6,562,071 B2 | 5/2003 | Jarvinen | |
| 6,589,281 B2 | 7/2003 | Hyde, Jr. | |
| 6,610,064 B1 | 8/2003 | Goble et al. | |
| 6,623,524 B2 | 9/2003 | Schmieding | |
| 6,673,115 B2 | 1/2004 | Resch et al. | |
| 6,712,823 B2 | 3/2004 | Grusin et al. | |
| 6,733,529 B2 | 5/2004 | Whelan | |
| 6,752,830 B1 | 6/2004 | Goble et al. | |
| 6,755,840 B2 | 6/2004 | Boucher et al. | |
| 6,780,188 B2 | 8/2004 | Clark et al. | |
| 6,878,166 B2 | 4/2005 | Clark et al. | |
| 6,887,271 B2 | 5/2005 | Justin et al. | |
| 7,022,124 B2 | 4/2006 | Takei et al. | |
| 7,033,364 B1 | 4/2006 | Walters et al. | |
| 7,229,448 B2 | 6/2007 | Goble et al. | |
| 7,285,121 B2 | 10/2007 | Braun et al. | |
| 7,309,337 B2 | 12/2007 | Colleran et al. | |
| 7,341,592 B1 | 3/2008 | Walters et al. | |
| 7,458,975 B2 | 12/2008 | May et al. | |
| 7,601,165 B2 * | 10/2009 | Stone ........................... 606/232 |
| 2001/0039455 A1 | 11/2001 | Simon et al. | |
| 2001/0044627 A1 | 11/2001 | Justin | |
| 2001/0047210 A1 | 11/2001 | Wolf | |
| 2001/0053934 A1 | 12/2001 | Schmieding | |
| 2002/0019635 A1 | 2/2002 | Wenstrom, Jr. et al. | |
| 2002/0058941 A1 | 5/2002 | Clark et al. | |
| 2002/0077631 A1 | 6/2002 | Lubbers et al. | |
| 2002/0087160 A1 | 7/2002 | Clark et al. | |
| 2002/0099381 A1 | 7/2002 | Maroney | |
| 2002/0111689 A1 | 8/2002 | Hyde, Jr. | |
| 2002/0111690 A1 | 8/2002 | Hyde | |
| 2002/0133153 A1 | 9/2002 | Hyde, Jr. | |
| 2002/0138148 A1 | 9/2002 | Hyde, Jr. | |
| 2002/0138149 A1 | 9/2002 | Hyde, Jr. | |
| 2003/0032961 A1 | 2/2003 | Pelo et al. | |
| 2003/0065332 A1 | 4/2003 | TenHuisen et al. | |
| 2003/0097179 A1 | 5/2003 | Carter et al. | |
| 2003/0105524 A1 | 6/2003 | Paulos et al. | |
| 2003/0163202 A1 | 8/2003 | Lakin | |
| 2004/0087953 A1 | 5/2004 | Singhatat et al. | |
| 2004/0092936 A1 | 5/2004 | Miller et al. | |
| 2005/0038426 A1 | 2/2005 | Chan | |
| 2005/0137704 A1 | 6/2005 | Steenlage | |
| 2005/0149187 A1 | 7/2005 | Clark et al. | |
| 2005/0177165 A1 | 8/2005 | Zang et al. | |
| 2005/0197662 A1 | 9/2005 | Clark et al. | |
| 2005/0203622 A1 | 9/2005 | Steiner et al. | |
| 2006/0229722 A1 | 10/2006 | Bianchi et al. | |
| 2008/0027443 A1 | 1/2008 | Lambert | |
| 2008/0228271 A1 | 9/2008 | Stone et al. | |

FOREIGN PATENT DOCUMENTS

| | | |
|---|---|---|
| FR | 2 684 543 | 6/1993 |

* cited by examiner

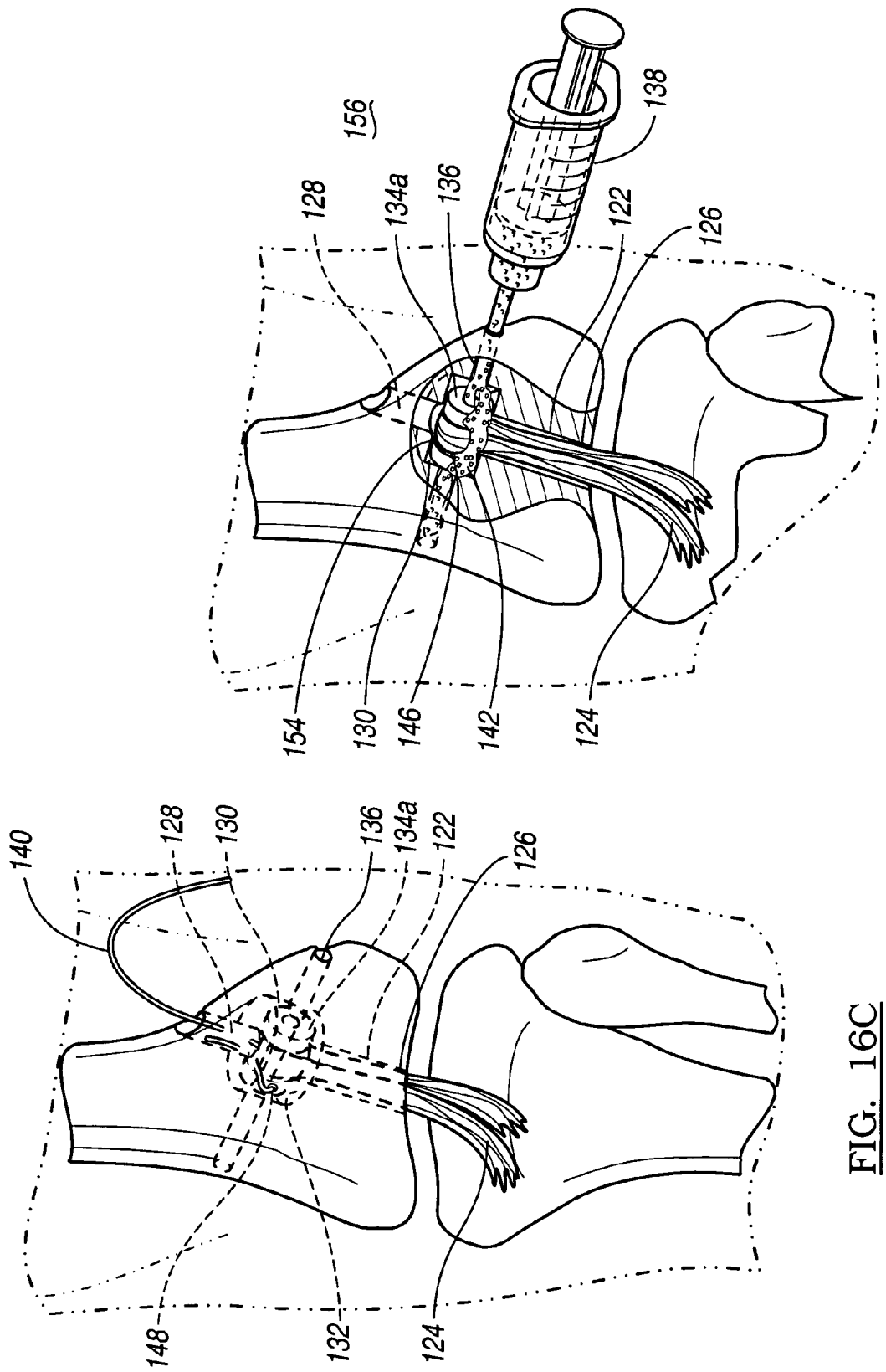

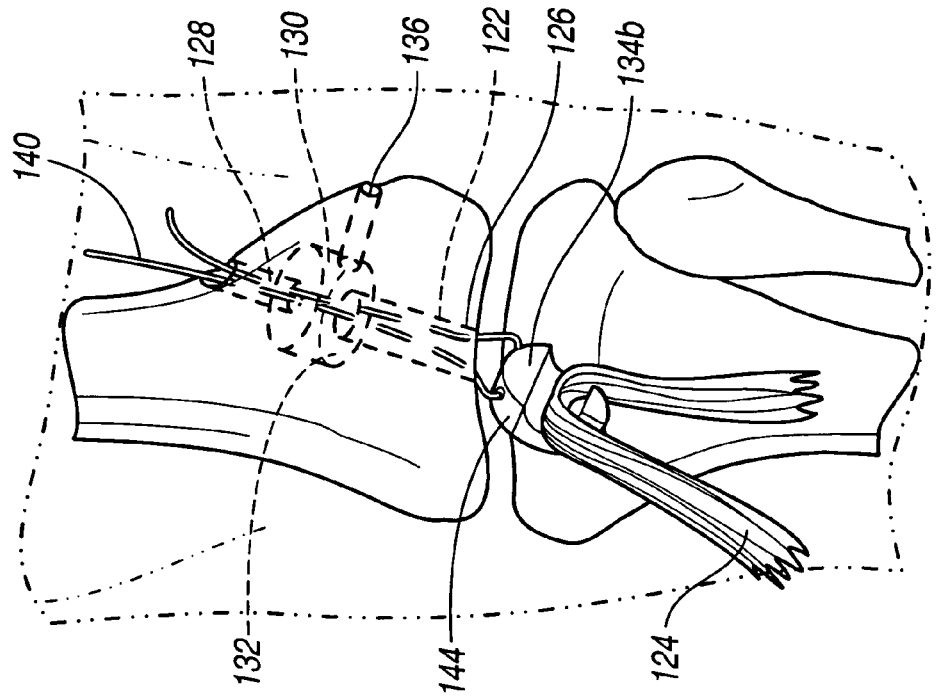
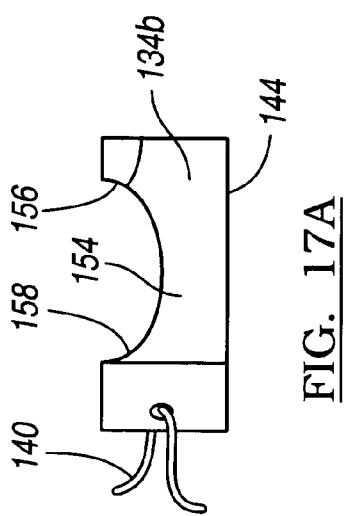
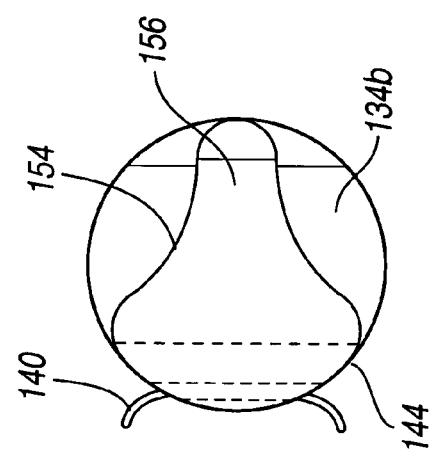

METHOD AND APPARATUS FOR GRAFT FIXATION

CROSS-REFERENCE TO RELATED APPLICATIONS

This application is a continuation-in-part application of U.S. patent application Ser. No. 10/686,236 filed on Oct. 15, 2003. The disclosure of the above application is incorporated herein by reference.

FIELD OF THE INVENTION

The present invention relates to endoscopic soft tissue replacement fixation. More particularly, the present invention relates to an apparatus and a method to reconstruct an anterior cruciate ligament with soft tissue replacements within a femoral tunnel.

BACKGROUND OF THE INVENTION

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

Currently, fascia lata soft tissue replacements are flexible strands which are affixed to a threaded stud and turned into the femoral tunnel. Unfortunately, this procedure may result in the soft tissue replacement being wrapped upon itself during insertion. Hamstring soft tissue replacements are also currently fixed over a screw in the tibial tunnel and fixed on the lateral femur. This technique requires the femoral tunnel to completely penetrate the femur. In addition, according to present procedures, fixation of the soft tissue replacement on the femoral side requires a large incision.

It has been difficult to insert and fasten a soft tissue replacement in a blind hole or tunnel. Attempts have been made to thread the soft tissue replacement through the tunnel and over an anchor, but with some difficulty. Thus far, the prior art has not developed a quick and efficient way to implant a soft tissue replacement over an implanted anchoring system.

While offering certain improvements in arthroscopic surgery to repair ligaments, the prior art may still be improved upon to overcome the limitations on the endoscopic hamstring soft tissue replacement fixation due, in many instances, to the weakness of the flexible strand used to span the gap between the tendon soft tissue replacement and the fixation post.

Other techniques attempt to use biological fixation to augment or replace mechanical fixation. While increasing fixation strength these techniques require time to fully realize their fixation potential. Additionally the techniques may take additional surgical time and resources that a purely mechanical fixation technique may not require.

SUMMARY OF THE INVENTION

An apparatus including a member that acts as a flexible strand insertion and guide rod is used to increase the simplicity and effectiveness of a soft tissue implant procedure. The member inserts a flexible strand, which has been preloaded onto the insertion rod, into a blind tunnel formed in a bone structure and provides a guide for first and second drill points or bits. Thus the member may be removed with the flexible strand already positioned in place to pull an implant into the blind tunnel over the first drill point and adjacent the second drill point. The second drill point is then removed, allowing the implant to be easily pulled over the first drill point. A cross or set pin is then pulled after the drill point into the drill hole to lock the implant in place.

A first embodiment includes an apparatus to position a flexible strand in a tunnel, having a diameter, formed in a bone while performing a surgery. The apparatus comprises a guide member extending along a first axis and having a first end and second end. The guide member includes a guide portion defining an area, extending from the first end and along the first axis. The guide portion includes a first leg and a second leg, the first leg and the second leg define a slot disposed therebetween, wherein the slot defines a first plane. The first leg further defines a first groove and the second leg defines a second groove; wherein the first groove extends along a distal end of the first leg and along a length of the first leg and the second groove extends along a distal end of the second leg and along a length of the second leg. The first groove and the second groove are adapted to receive the flexible strand. The apparatus further has a second guide member fixed parallel to the first member. The second member has a pair of guide holes configured to guide first and second adjacent drill points.

A second embodiment of the apparatus includes an apparatus to place a flexible strand in a tunnel, having a diameter, formed in bone while performing a surgery. The apparatus comprises a first member having a first end and a second end spaced apart. The first end defines a slot, adapted to guide an instrument, wherein the slot lies in a first plane. The first end further defines a groove, wherein the groove lies in a second plane. The first plane and the second plane intersect. A second member having a first end and a second end, the second member defines first and second passages positioned adjacent the first end. The first member extends adjacent to the second end of the second member; wherein the first end of the first member and the passage are generally aligned.

The apparatus allows a method of performing an implant procedure. A method of surgically implanting a soft tissue replacement for attaching two bone members comprises inserting an insertion rod having a flexible strand pre-loaded on the insertion rod into a first tunnel. Next, forming second and third tunnels transverse and through the first tunnel and the insertion rod with a tool bit. Next, retaining the flexible strand within the first tunnel. The method also includes removing the insertion rod from the second tunnel and retracting the flexible strand.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 12 and 13 represent the insertion of the soft tissue into a femoral tunnel shown in FIG. 10;

FIGS. 13 and 14 represent the insertion of a soft tissue implant according to the teachings of a second embodiment of the invention;

FIGS. 16a through 16d represent the insertion of a soft tissue implant according to another embodiment of the invention;

FIGS. 17a and 17b represent side and end views of a soft tissue implant according to the teachings of the present invention;

FIG. 18 represents the insertion of soft tissue using a soft tissue implant shown in FIGS. 17a and 17b;

DETAILED DESCRIPTION OF THE PREFERRED EMBODIMENTS

The following description of the embodiments is merely exemplary in nature and is in no way intended to limit the invention, its application, or uses. Moreover, while the present invention is discussed in detail below with regard to ACL reconstruction, those skilled in the art will recognize the other types of soft tissue fixation may employ the present invention.

Figure 1:
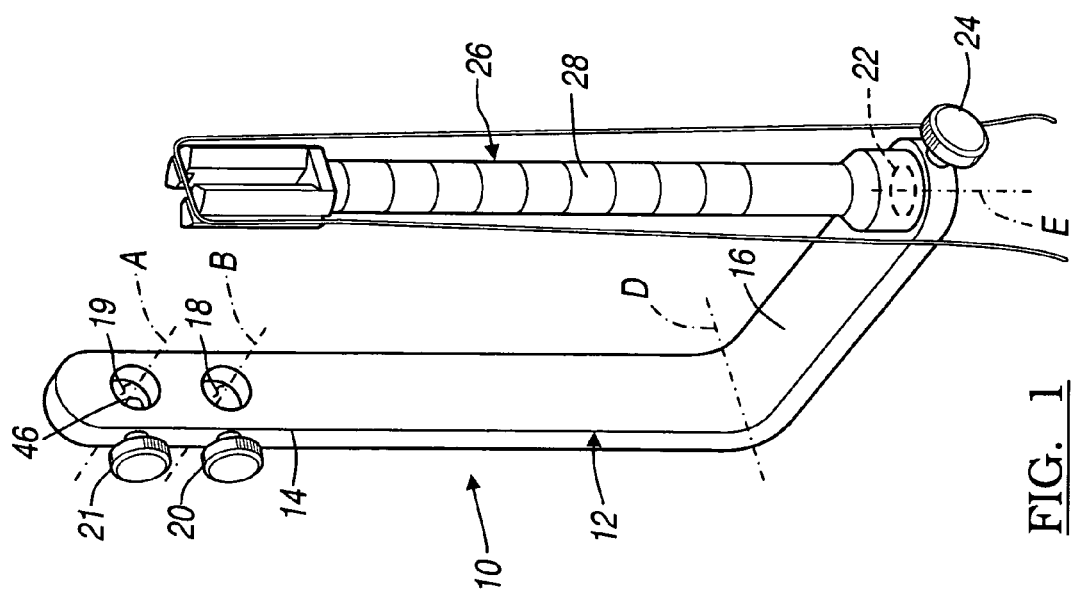
FIG. 1 is a perspective view of the bone insertion rod affixed to a U-Guide.

Referring to, FIG. 1, a guide apparatus 10, which may be generally U-shaped, includes an L-shaped retaining bar or L-guide 12 that includes two portions or legs, a first portion 14 and a second portion 16, that is substantially perpendicular to the first portion 14. The first portion 14 defines a first guide section 18 and a second guide section 19, formed transversely through the first portion 14. The guide section may be passage through or transverse to the first portion 14 such as a bore wherein the guide section ledge would be a bore ledge. A pair of set screws 20 and 21 are provided to create a locking mechanism for the guide sections 18 and 19. The second portion 16 defines a bore 22 formed transversely through the second portion 16. A set screw 24 is also provided to create a locking mechanism for the bore 22. The L-guide 12 is shown in an L-shape, however, it will be understood the L-guide 12 may be any appropriate form. Generally, however, the axes defining the guide section 18 and the bore 22 are orthogonal. Therefore, the first and second axis A and B of the guide section 18 should intersect the second axis E of the bore 22 at a right angle.

An insertion or guide rod 26 is adjustably held in the bore 22 and locked in place with the set screw 24. With continuing reference to FIG. 1 and further reference to FIG. 2, the insertion rod 26 includes a body portion 28. The body portion 28 is substantially cylindrical and formed around a longitudinal axis C. The body portion 28, which is generally a solid, may also taper towards the guide portion 36 (described herein). Also, the body portion 28 may include depth indicia 29 to give a visual indication of the depth of the insertion rod 26 into a patient.

Extending from a first end of the body portion 28 is an L-Guide engaging portion 30 which includes a notch or projection 32 that is received in the second portion 16 of the L-Guide 12 to ensure proper orientation of the insertion rod 26 to the L-Guide 12. The notch 32 on the insertion rod 26 is keyed to be received on to a portion of the second portion 16. The insertion rod 26 further includes a collar 34, to ensure that the insertion rod 26 is held at a predetermined depth in the L-Guide 12 and to further ensure proper orientation of the insertion rod 26 relative to the L-Guide 12.

A guide portion 36 extends from a second end of the body portion 28. The guide portion 36 includes two generally parallel legs 38 and 40 and a shoulder 41. Each leg 38, 40 extends from the body portion 28 along axis C, though offset therefrom. The two legs 38, 40 define a slot 42, where the slot 42 extends substantially the distance of the two legs 38, 40 and meet at the shoulder 41. Also formed in each of the legs 38, 40 is a flexible strand groove 44. The flexible strand groove 44 may be any appropriate depth, but exemplary is substantially equal in depth to the diameter of a cord or flexible strand thread or suture to be used with the apparatus 10.

The insertion rod 26 may be any desired length. Preferably, however, the distance between the collar shoulder 34 and the shoulder 41 is equal to the distance between a first end of the first portion 14, generally represented by line D, and the guide section 19. In this way, the guide section ledge 19 and the slot 42 are generally equidistant from the second portion 16. Therefore, any instrument received through the guide section 19 would remain substantially parallel to the second portion 16 when it passed through the slot 42.

The flexible strand groove 44 is placed orthogonally to the slot 42 so that a cord, such as a flexible strand, may be placed in the flexible strand groove 44 to form an enclosed passage for any device that may be placed through the slot 42. In this way, a device such as a K-Wire (described herein), when inserted through the slot 42 has a flexible strand looped over the K-Wire. It will be understood, however, that the flexible strand groove 44 may be formed at any orientation relative to the slot 42 as long as a flexible strand placed in the flexible strand groove 44 will overlay the slot 42.

The notch 32 ensures that the insertion rod 26 is properly oriented with the L-Guide member 12 of the U-guide apparatus 10. In particular, the slot 42 is preferably aligned with the guide sections 18 and 19. The set screw 24 tightens against the L-Guide engaging portion 30 to ensure that the insertion rod 26 does not move during a surgical procedure. Also, this ensures the proper keyed fit of the notch 32 into the second portion 16 so that the guide section 18 and the slot 42 are properly aligned. This ensures that the instrument received through the apparatus 10 is aligned. It will be understood, however, that any appropriate means may be used to secure the insertion rod 26 to the L-Guide member 12 of the apparatus 10.

Referring to the remaining FIGS. 3-11, an exemplary method for using the apparatus 10, including the insertion rod 26 is described. It will be understood that although the apparatus 10 is described in the use of an Anterior Cruciate Ligament (ACL) replacement, any appropriate surgery may be performed with the apparatus 10 which would require its attributes.

Figure 3:
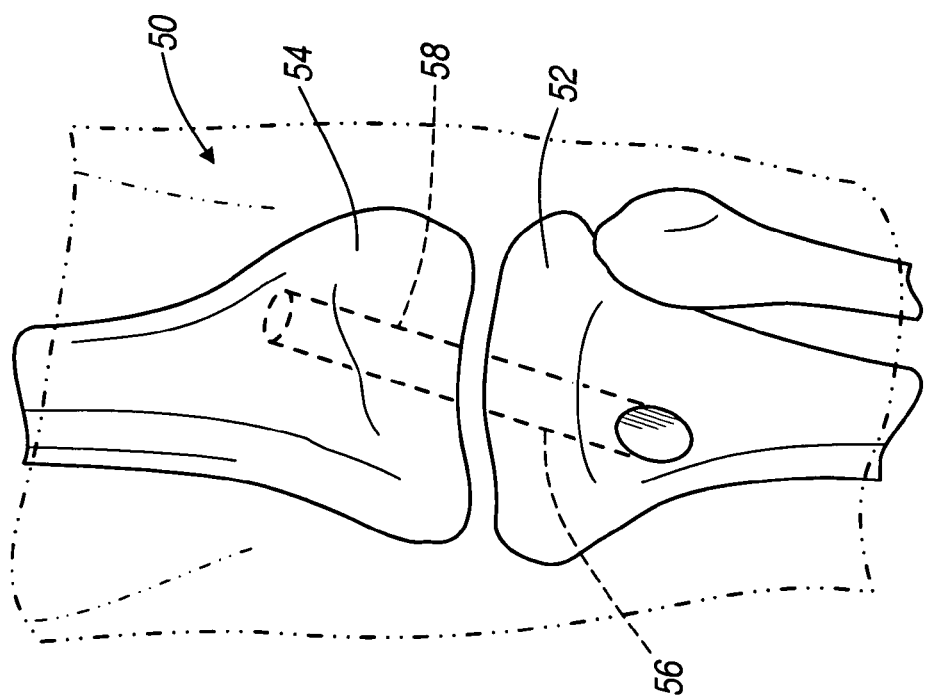
FIG. 3 is an exemplary view of a knee prepared for insertion of the insertion rod.

With particular reference to FIG. 3, a knee 50 generally includes at least a tibia 52 and a femur 54 surrounded by soft tissue 55. The knee 50 is initially prepared by forming a tibial tunnel 56 and a femoral tunnel 58 which are substantially in line with one another such that a straight and solid object could engage both the tibial tunnel 56 and the femoral tunnel 58 without a substantial amount of stress when the knee is placed in flexion between about 30 degrees and 110 degrees. It is understood that incisions must first be made in the soft tissue 55 surrounding the tibia 52 such that a tool may engage the tibia 52 and the femur 54 to form the tibial tunnel 56 and the femoral tunnel 58. Any suitable tool may produce the respective tunnels 56, 58 such as a pneumatic or electric drill or reamer. It is also understood that the femoral tunnel 58 is a blind tunnel. A blind tunnel is a tunnel which includes an entrance but no discernable exit, rather a blind tunnel terminates below the surface of the femur 54.

The size of the tibial tunnel 56 and the femoral tunnel 58 depends upon the size of the soft tissue replacement (described further herein) to be implanted into the patient. The larger the replacement needed, the larger the diameter of the tibial tunnel 56 and the femoral tunnel 58. The tibial tunnel 56 and femoral tunnel 58 may be of any required diameter, but are generally between about 5 and 18 millimeters. It would be understood, however, that if a larger diameter replacement is necessary, then larger diameter tunnels 56, 58 may be produced in the tibia 52 and femur 54 to receive the implant. Additionally, smaller tunnels 56, 58 may be used if only a smaller implant is necessary. In addition, the largest area of the insertion rod 26 will have a diameter substantially equal to the diameter of the tibial tunnel 56 and femoral tunnel 58. For example, if the insertion rod 26 was produced so that the guide portion 36, in particular the shoulder 41, form the largest diameter of the insertion rod 26, then the outside diameter of the guide portion 36 would be substantially equal to diameter of the tibial tunnel 56 and the femoral tunnel 58. Also, the body portion 28 may have a lesser diameter, or a taper towards the shoulder 41, to ease insertion and removal of the insertion rod 26. This ensures that the insertion rod 26, and particularly the slot 42, are substantially centered in the femoral tunnel 58 for the remaining procedure.

Figure 2:
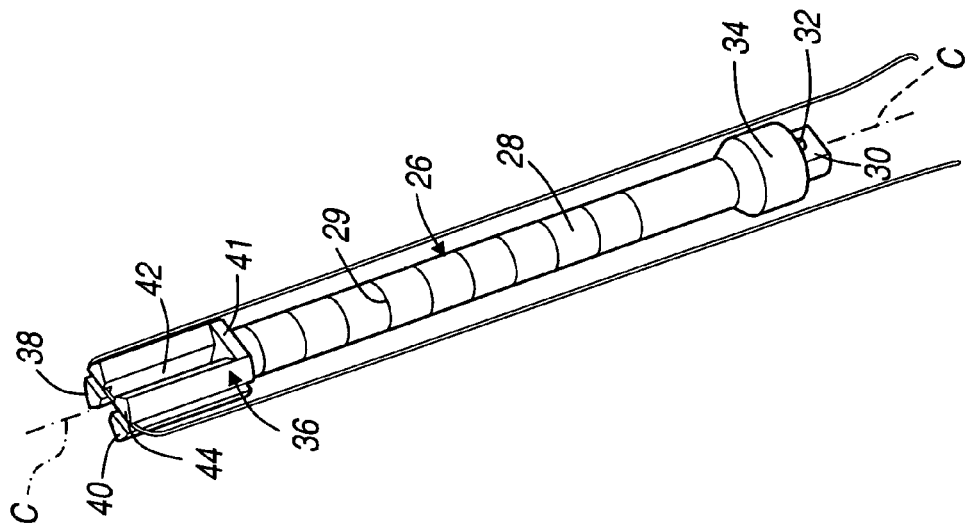
FIG. 2 is a perspective view of bone insertion rod not affixed to the U-Guide.
Figure 4:
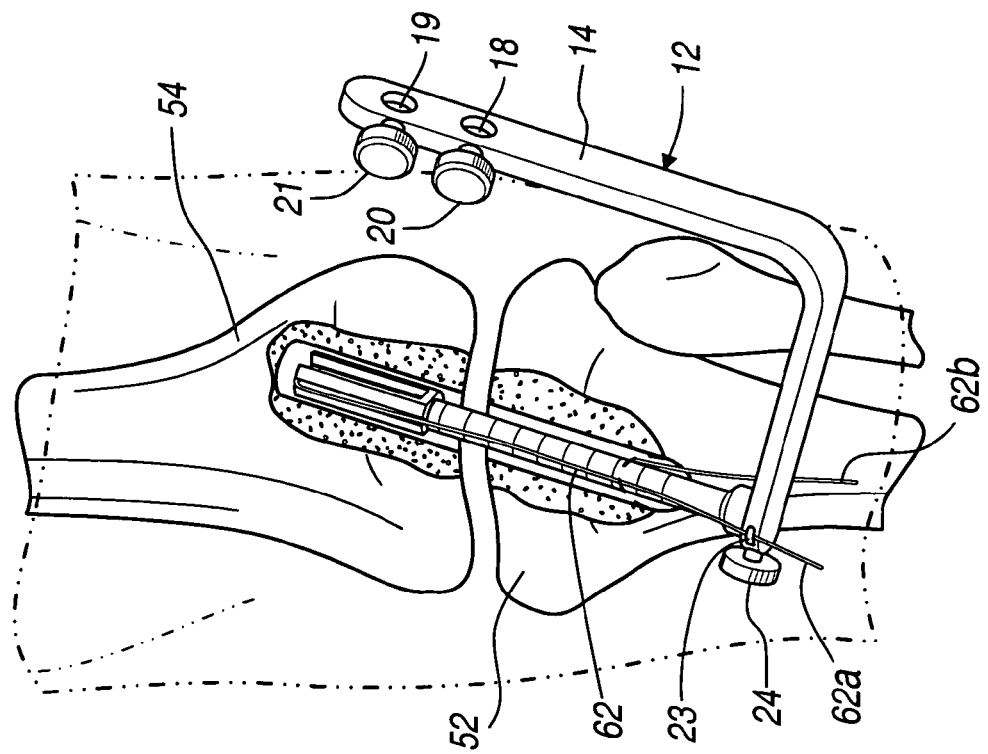
FIG. 4 is a perspective view of the insertion rod and U-Guide inserted into the tibia and femur tunnels with the flexible strand in place.

A flexible strand 62, having a trailing end 62a and a leading end 62b, is placed or pre-loaded into the flexible strand groove 44 and then the insertion rod 26 is inserted through the tibial tunnel 56 and into the femoral tunnel 58, as best shown in FIG. 4 (see also FIGS. 1 and 2). The flexible strand 62 may be any generally known strand suitable to the purpose such as a mono- or poly-filament suture, a flexible wire, or cord made of any suitable material. The flexible strand groove 44 allows the flexible strand 62 to be inserted through the tunnels 56, 58 without engaging the walls of the tunnels 56, 58. Generally the depth of the flexible strand groove 44 is at least equal to the diameter of the flexible strand 62. The flexible strand 62 is placed so that it reaches substantially to the end of the femoral tunnel 58 and the slot 42 creates an opening through the center of the femoral tunnel 58 through which an instrument may pass, while not interrupting the flexible strand 62 which has been inserted into the femoral tunnel 58 by the insertion rod 26. The flexible strand 62 is caught in the flexible strand notch 23. The flexible strand 62 is held in position during the insertion of the insertion rod 26 into the tunnels 56, 58 and during the remaining surgical procedure by the flexible strand notch 23. Any suitable means may be used to hold the flexible strand 62 in place relative to the L-Guide member 12 of the apparatus 10. The flexible strand notch 23, which holds the flexible strand 62 with friction, is merely exemplary of one appropriate means to hold the flexible strand 62 in place.

Figure 5:
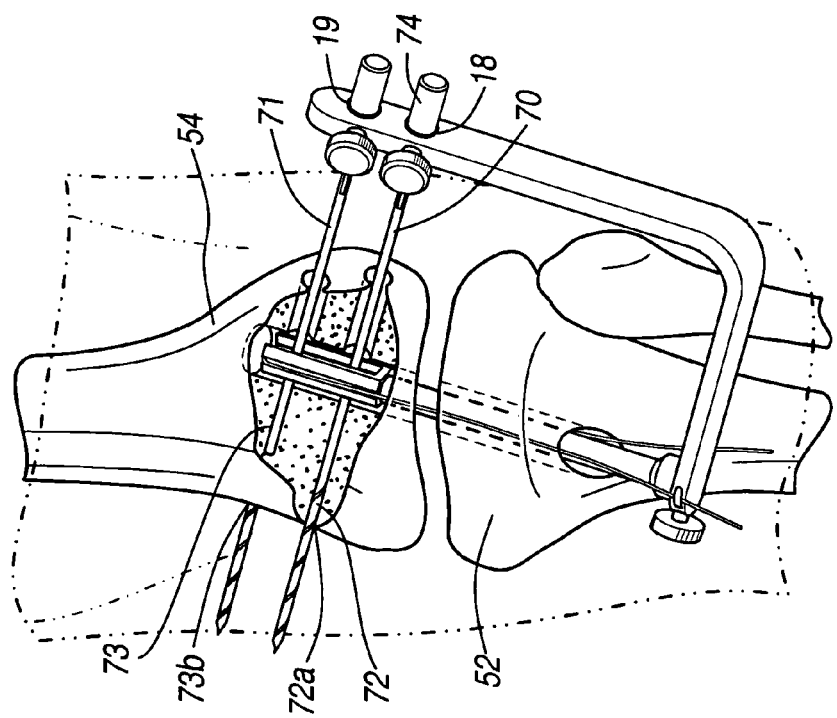
FIG. 5 is a view of the U-Guide and insertion rod in place with a pair of K-Wire Drill Points forming a transverse tunnel.

Referring generally to FIG. 5, once the insertion rod 26 has been inserted into the femoral tunnel 58, so that the flexible strand 62 is positioned properly, a device, such as a first drill bit or point 70 is used to produce a transverse tunnel 72 in the femur 54. The transverse tunnel 72 is formed transversely to the femoral tunnel 58 by using the first guide section 18. The second guide 19 is used to form a second transverse tunnel 73 using a second drill bit or point 71. The transverse tunnel 72 will include an insertion point 72a and an exit point 72b. It will be understood that an incision must first be made in the soft tissue 55 surrounding the femur 54, so that the drill bit or points 70 and 71 may engage the femur 54 to form the transverse tunnel 72. The drill points 70 and 71 may be powered by any appropriate device known in the art such as an electric or pneumatic drill. Furthermore, additional guide units or bullets 74, such as the U-Guide bullet produced by Arthotek, Inc. of Warsaw, Ind., may be used to ensure the proper orientation and depth of the drill points 70 and 71. The guide bullet 74 is inserted into the guide sections 18 and 19 and held in place with the set screws 20 and 21 to ensure the drill points 70 and 71 are properly aligned with the slot 42 when producing the transverse tunnels 72.

The transverse tunnels 72 and 73 are produced through the entire width of the femur 54 so that the drill points 70 and 71 exits the femur 54 producing the exit points 72b and 73b. This allows the drill points 70 and 71 to be removed through the exit points 72b and 73 at the appropriate time. While the apparatus 10 is still in place, a cannulated reamer (not shown) enlarges a portion of the transverse tunnel 72. The reamed tunnel 75 receives the pin 84 (described herein). The reamed tunnel 75 does not extend the length of the transverse tunnel 72. The second drill point 71 forms a removable suture bearing surface 76, while the first drill point 70 has a soft tissue bearing surface 77.

Figure 6:
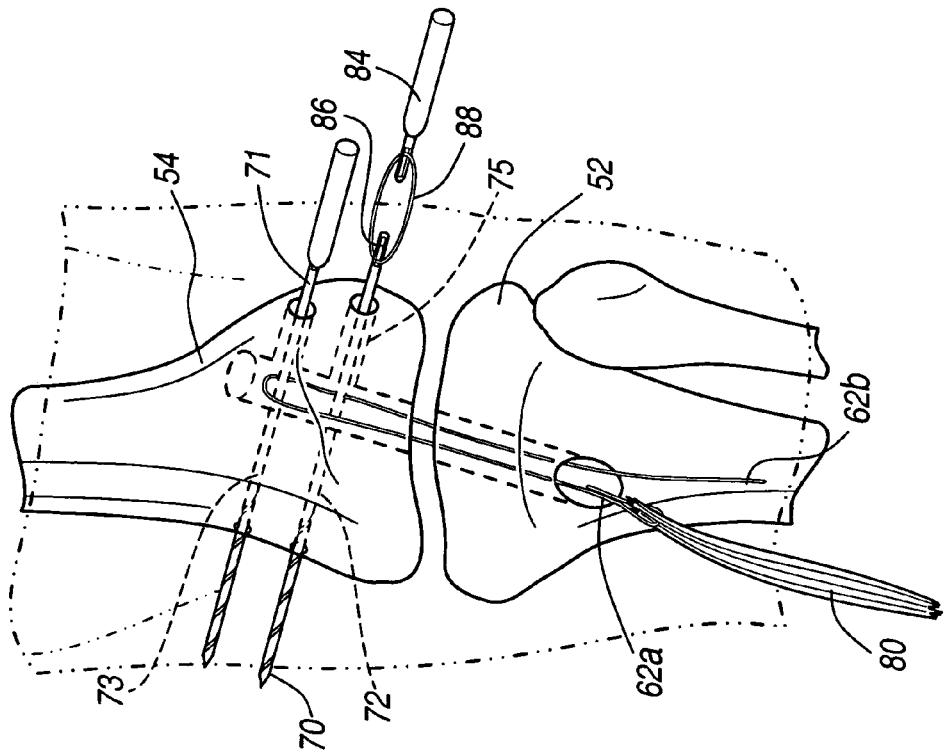
FIG. 6 is perspective view of the first and second K-Wire Drill Points with the flexible strand affixed to a soft tissue replacement and draped over the second K-Wire Drill Point.

After the reamed tunnel 75 is produced, the apparatus 10, is removed as particularly shown in FIG. 6. Once the apparatus 10 has been removed, the drill point 70 remains in the transverse tunnel 72. A soft tissue replacement 80 is affixed to the trailing end 62a of the flexible strand 62. The soft tissue replacement may be any suitable replacement such as a hamstring portion, an allograft tissue replacement, a xenograft tissue replacement, or an artificial soft tissue replacement which may be produced from materials such as polymers or metal.

Figure 7:
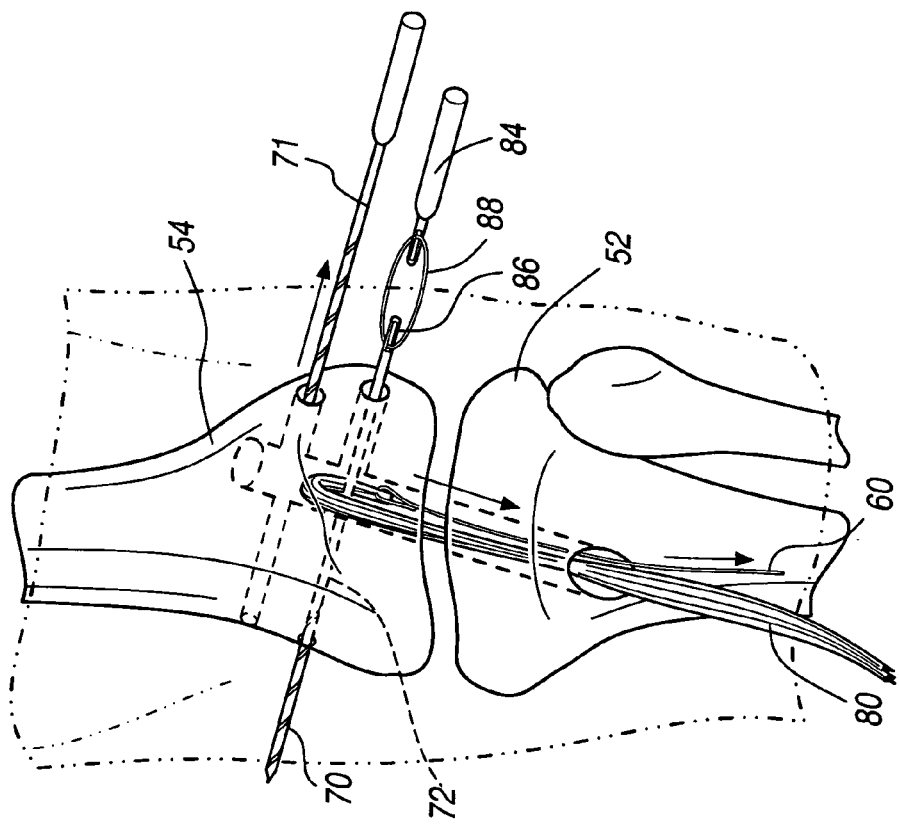
FIG. 7 depicts the second K-Wire Drill Point removed with the soft tissue replacement draped over the first K-Wire Drill Point.
Figure 8:
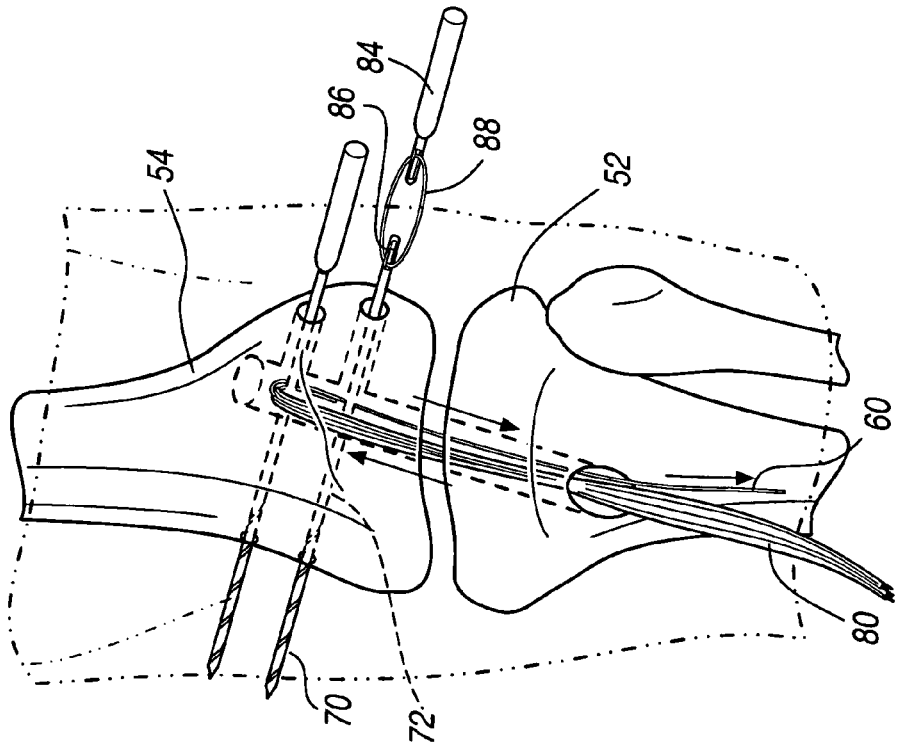
FIG. 8 is a perspective view of the soft tissue replacement pulled over the K-Wire and out through the tibial tunnel.

As shown in FIG. 7, after the soft tissue replacement 80 has been affixed to the trailing end 62a, the leading end 62b of the flexible strand 62 is pulled over the suture bearing surface 76 drawing the soft tissue replacement 80 first through the tibial tunnel 56 and then through the femoral tunnel 58 adjacent to and preferably over the first drill point 70 and up to the second drill point 71. At this point, the second drill point and suture bearing surface 76 is removed and the flexible strand and soft tissue is pulled to pull the soft tissue over the first drill point 70 and associated soft tissue bearing surface 77, back down the femoral tunnel 58, and out through the tibial tunnel 56. This produces a loop of the soft tissue replacement 80 over the soft tissue bearing surface 77 of the first drill point 70 inside of the femoral tunnel 58. After being looped over the first drill point 70, the two free ends 80a and 80b of the soft tissue replacement 80 extend from the tibial tunnel 56 adjacent to the tibia 52.

After the soft tissue replacement 80 has been looped over the first drill point 70, an ACL cross pin or pin 84 is pulled into place in the reamed tunnel 75. The drill point 70 generally includes an eyelet 86 which will allow the attachment of the pin 84 to the drill point 70. Generally, the pin 84 is attached to the eyelet 86 through a second flexible strand 88 or other appropriate means. After the pin 84 is attached to the eyelet 86, the drill point 70 is pulled through the transverse tunnel 72, through the loop of the soft tissue replacement 80 and out the exit point 72b. This pulls the pin 84 into position and fixes it within the transverse tunnel 72, as particularly shown in FIG. 9. Once the pin 84 has been fixed in place in the transverse tunnel 72, the attached flexible strand 88 may be cut or otherwise disengaged from between the eyelet 86 and the pin 84. The drill point 70 is then freely removed from the transverse tunnel 72. This leaves the pin 84 lodged into the transverse tunnel 72 which may be locked in place with either portions of the pin 84 or through any other appropriate locking means. Although any appropriate means may be used to hold pin 84 in the reamed tunnel 75, the pin 84 may include a square end to hold pin 84 in place. The pin 84 may also be threaded such as the device described in U.S. Pat. No. 5,674,224 entitled "Bone Mulch Screw Assembly For Industrial Fixation of Soft Tissue Soft tissue replacements And Method For Using Same" to Stephen M. Howell et al. incorporated herein by reference.

Figure 10:
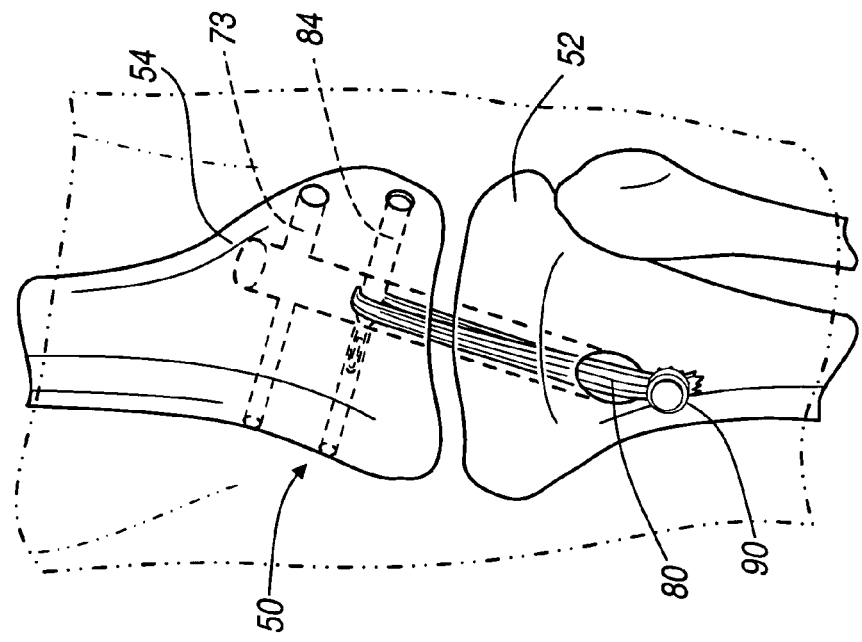
FIG. 10 is a view of the knee with an ACL replacement having its free ends affixed to the tibia and the femoral end affixed over the ACL Cross Pin.
Figure 9:
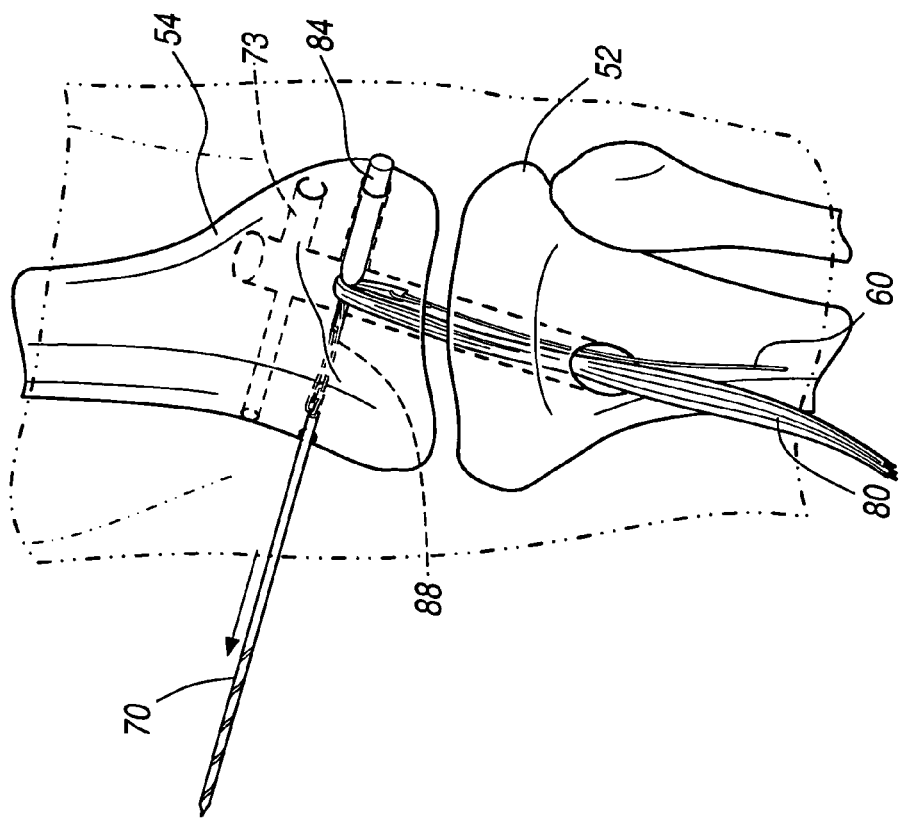
FIG. 9 is a perspective view of the soft tissue replacement in place and the ACL Cross Pin set in place in the transverse tunnel in the femur.
Figure 11:
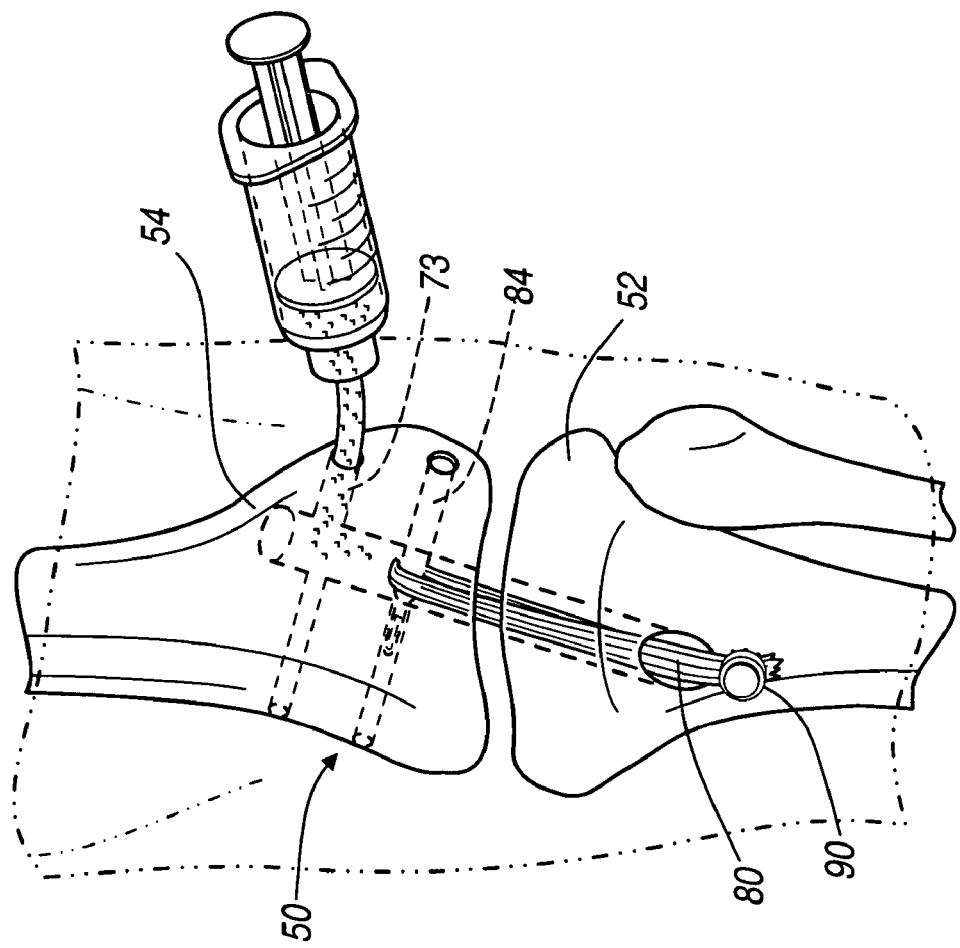
FIG. 11 represents the insertion of bone cement into the femoral tunnel shown in FIG. 1.
Figure 13:
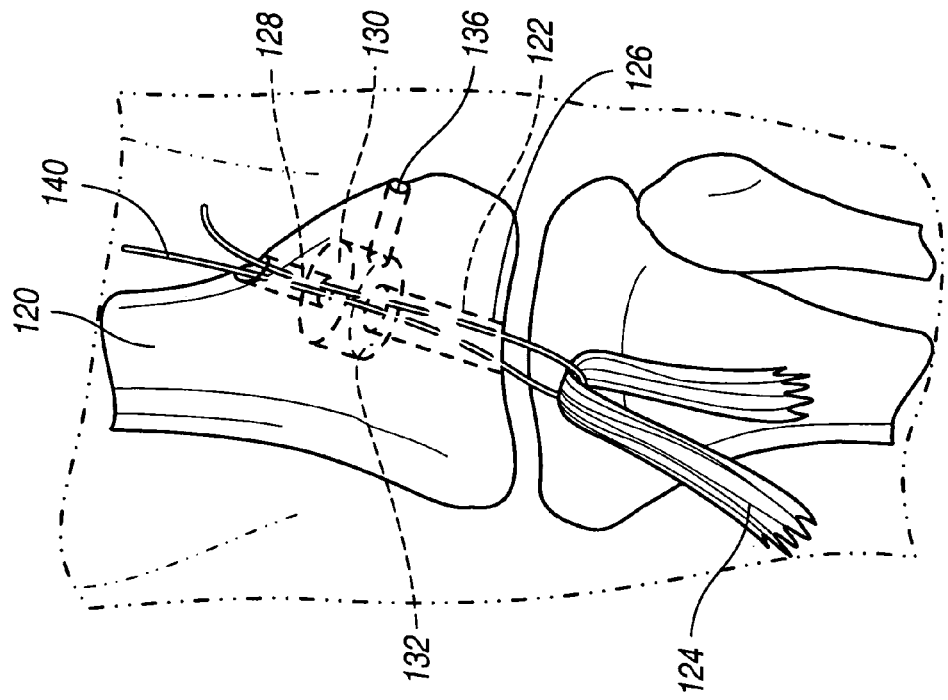

As shown in FIG. 10, the second transverse tunnel 73 forms an aperture which can be used to inject biologic materials such as platelets, bone chips, or allograph materials into the tunnel 56. Additionally, the second transverse passage 73 can be used to inject bone cement into the femoral tunnel 58 and about pin 84.

Because the pin 84 has been lodged in the transverse tunnel 72, and the soft tissue replacement 80 is looped over the pin 84, only the free ends 80a and 80b need to be secured to the tibia 52 to complete the implantation. A staple 90 is used to affix the free ends 80a and 80b of the soft tissue replacement 80 to the tibia 52, as best shown in FIG. 10. It will be understood, however, that any appropriate means may be used to affix the free ends 80a, 80b to the tibia 52 such as U.S. Pat. No. 5,674,224 entitled "Bone Mulch Screw Assembly For Industrial Fixation of Soft Tissue Soft tissue replacements And Method For Using Same" to Stephen M. Howell et al.; U.S. Pat. No. 6,280,472 B1 entitled "Apparatus And Method For Tibial Fixation Of Soft Tissue" to James A. Boucher et al.; and U.S. Pat. No. 5,931,869 entitled "Apparatus And Method For Tibial Fixation Of Soft Tissue" to James A. Boucher et al. each incorporated herein by reference. Once the free ends 80a and 80b of the soft tissue replacement 80 are affixed to the tibia 52, the soft tissue replacement 80 securely attaches the tibia 52 and the femur 54 substantially as a natural ACL would.

It will be understood that any appropriate means may be used to affix the soft tissue replacement 80 in the femoral tunnel 58. The pin 84 is merely exemplary of any appropriate device to affix the soft tissue replacement 80 in the femoral tunnel 58. Any commonly known screw or other fixation device may be used to fix the soft tissue replacement 80 in the femoral tunnel 58. It will also be understood that the soft tissue replacement 80 may be pulled over the pin 84 after the pin 84 has been lodged in the transverse tunnel 72. In particular, if the pin 84 is smooth, the soft tissue replacement 80 may be pulled over the pin 84 without damaging the soft tissue replacement 80 itself. The drill point 70 is simply removed from the transverse tunnel 72 before the soft tissue replacement 80 is pulled into the femoral tunnel 58.

It will also be understood that the method for performing the described procedure may be altered but remain within the scope of the presently claimed invention. For example the flexible strand 62 may looped over the insertion rod 26 such that the two free ends 62a and 62b are on one side and a loop of the flexible strand is formed on the other side of the insertion rod 26. Thus the soft tissue replacement 80 may be affixed to both free ends 62a and 62b or placed through the loop and then pulled over the insertion rod 26.

Figure 12:
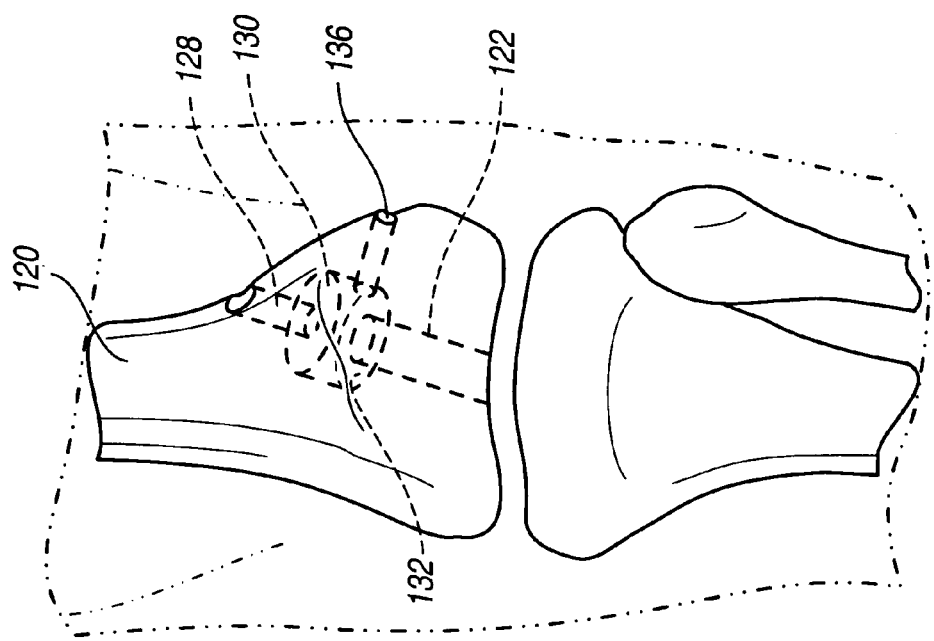
FIG. 12 is a view of a knee joint having a prepared femur accordance to the teachings of an embodiment the present invention.

Referring to FIG. 12, a prepared femur 120 is shown. Bored into the femur is a femoral tunnel 122 configured to accept an ACL 124. The femoral tunnel 122 has a first portion 126 having a first diameter and a second portion 128 having a second diameter which is smaller than the first diameter. The second portion can be co-axial with the first portion. Disposed between the first and second portions is a locking cavity 130. The locking cavity 130 is configured to provide a positive bearing surface 132 which, as described below, functions as a bearing surface for a locking member 134.

Generally perpendicular to the femoral tunnel is a transverse tunnel 136 which is used for the introduction of biocompatible or biological materials. As further described below, the materials can be injected into the femoral tunnel 122 through the transverse passage by the use of a syringe 38 or similarly configured injection device.

Figure 15:
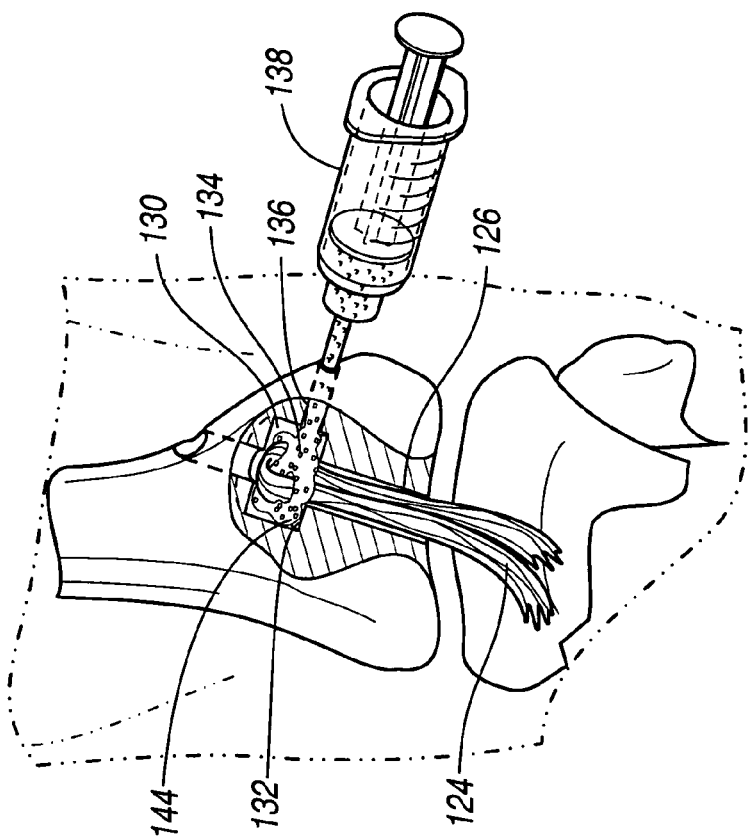
FIG. 15 represents the insertion of bone cement into the femoral tunnel shown in FIG. 12.
Figure 14:
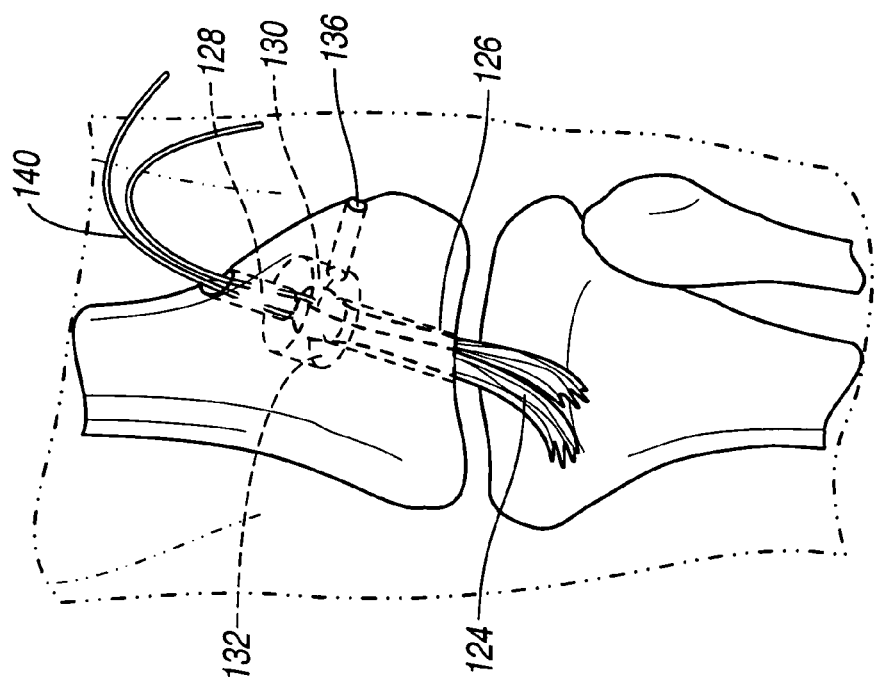

As shown in FIGS. 14 and 15, the ACL 124 is coupled to a suture 140, which is fed into the femoral tunnel 122. The suture 140 can be fed directly though the femoral tunnel 122, or can be inserted into the tunnel 122 using a guide rod (not shown). The ACL 124 is then pulled up through the femoral tunnel 122 to a point that the ACL 124 reaches the locking cavity 130. It is envisioned that the suture 140 can be equipped with indicia which will signal the physician when the ACL 124 has been drawn a sufficient distance into the femoral tunnel 122 so as to position a portion of the ACL 124 into the locking cavity 130.

As best seen in FIG. 15, liquid locking cement 142 is injected into the locking cavity through the transverse tunnel 136 so as to completely surround the ACL 124 and substantially fill the locking cavity 130. It is envisioned that this locking cement 142 is a fast curing cement which quickly hardens into a locking member 134 to lock the ACL 124 into the locking cavity 130. Additionally, the cement can include either morselized allograph materials, xenograft materials, platelets, synthetic bone cement, as well as other types of orthopedic graft materials such as a 50/50 CaP/CaS material and combinations thereof. The formed locking member 134 defines a pair of surfaces 144 which engage the bearing surfaces of the locking cavity.

It is further envisioned that the locking cement 142 be of sufficient strength so that when the ACL 124 is axially loaded under normal loading, the ACL 124 does not become disconnected from the formed locking member 134. Further, the locking anchor member 134 is of sufficient strength so as to not to deform or fracture when loaded by the bearing surface 132 of the locking cavity 130. After the cement 142 is cured, the remainder of the ACL 124 is then formed into a canal formed in the tibia as is known in the art. The ACL 124 is then fixed to the tibia.

Figure 16B:
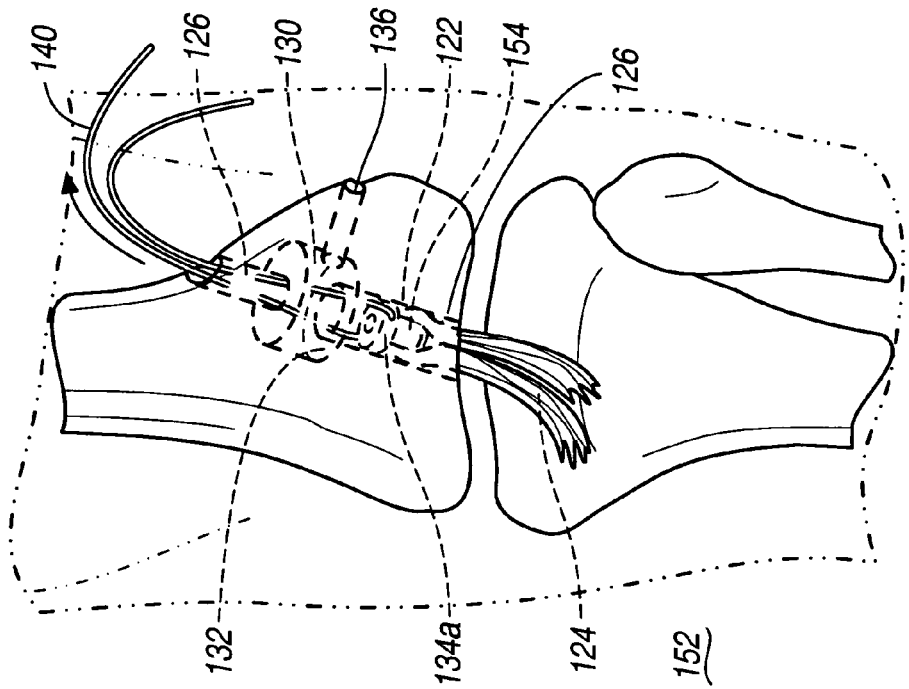
Figure 16A:
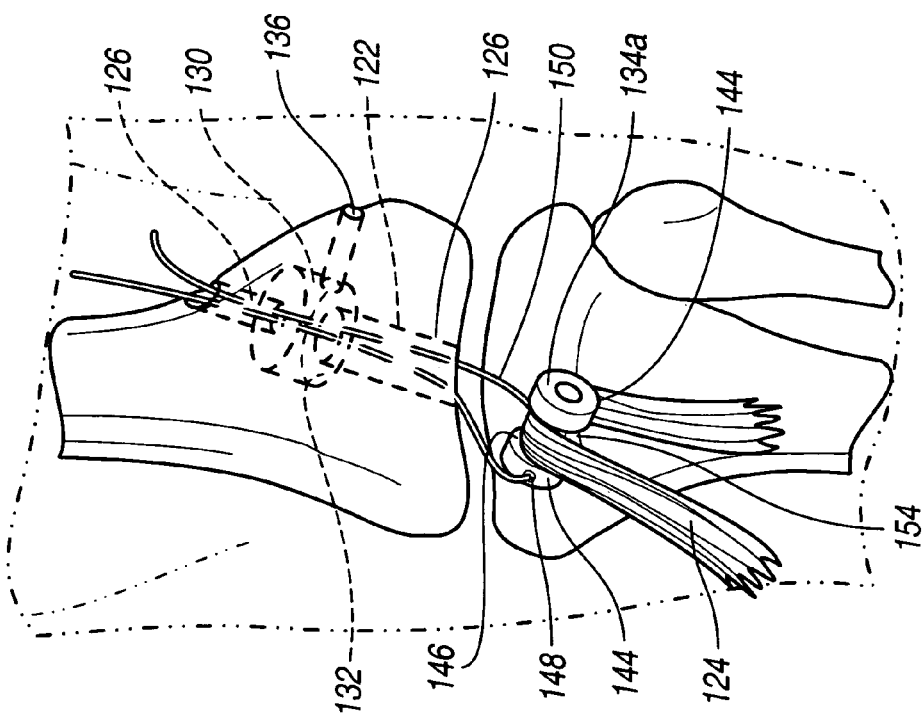

FIGS. 16a and 16b represent another embodiment of the invention. Coupled to a suture 140 is a one piece cylindrical biocompatible anchor member 134a. The anchor member 134a defines an ACL coupling slot 146, which functions as a hook to pull the ACL 124 into the locking cavity 130. The anchor member 134*a* further defines a suture retaining bore 148 passing through a portion of the cylindrical member 134, the suture retaining bore 148 is operable to receive the mid-portion of the suture or flexible strand 140. The locking member has a first profile or dimension which allows insertion of the locking member 134 through the femoral tunnel 122 and a second profile or dimension which allows engagement with the positive locking surface 132 upon rotation of the locking member 134 within the cavity 130.

As shown in FIGS. 16*b*-16*d*, the suture 140 is fed into and drawn up through the femoral tunnel 122. The biocompatible anchor member 134*a* and coupled ACL 124 is then pulled up through the femoral tunnel 122 to a point that the biocompatible locking member 34*a* and accompanying ACL 124 reaches the locking cavity 130. Generally, the locking member 134*a* is then rotated within the locking cavity 130 so as to lock the ACL 24 into the locking cavity 130. The locking member 134*a* further defines a first curved bearing surface 150 which supports the ACL 124 when the anchor is in a first orientation 152 and a second bearing surface 154 which supports the soft tissue implant when the anchor has been rotated into a second locked orientation 156. The locking member additionally defines a pair of bearing surfaces which engages the bearing surfaces of the locking cavity.

As best seen in FIG. 16*d*, liquid locking cement 142 may be optionally injected into the locking cavity 130 through the transverse passage 136 so as to completely surround the locking member 134*a* and ACL 124 so as to partially fill the locking cavity. The locking member 134*a* can have an optional through bore 153 which accepts and facilitates the flow of the liquid locking cement 142 to enhance the coupling of the ACL 124. As previously mentioned, it is envisioned that this locking cement 142 is a fast curing cement which quickly hardens into a structure to lock the locking member 134*a* and ACL 124 into the locking cavity 130.

The locking member 134 can also be formed of bioresorbable material. The use of various resorbable materials, typically in the form of various orthopedic devices, in connection with the treatment of various bone deformities, especially fractures, is well known in the art. These resorbable materials also referred to as bioresorbable, biodegradable, absorbable, and bioabsorbable devices, have enabled the medical community to achieve excellent surgical results, even under difficult clinical conditions.

The main benefit of using resorbable materials is that they are generally as strong as conventional metallic materials and resorb into the body over a generally predictable time period once a sufficient level of healing has occurred, for example, at the junction of a bone fracture, thus negating the need for subsequent removal of the material.

One exemplary resorbable material of particular interest is marketed by Biomet, Inc. (Warsaw, Ind.) under the tradename LACTOSORB®. LACTOSORB® is an absorbable co-polymer synthesized from all-natural ingredients: 82% L-lactic acid and 18% glycolic acid, unlike the homopolymers in common use such as 100% poly-L-lactic acid (PLLA) or 100% polyglycolic acid (PGA), LACTOSORB® copolymer is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of it's strength for six to eight weeks, which is appropriate for healing, but not so long as to raise concerns about long-term stress shielding of bone.

FIGS. 17 through 17*b* represent another embodiment of the invention. The ACL anchor 134*b* shown is specifically configured to draw the ACL 124 into the femoral tunnel 122 without causing interference between the ACL 124 and the sides of the tunnel. The ACL anchor 134*b* has a saddle bearing surface 154. The saddle bearing surface 154 defines a first seat 156 which bears the ACL while it is being drawn in to the femoral tunnel 122. The saddle bearing surface 154 also defines a second bearing surface 158, which functions as a bearing surface when then the locking member is rotated into its engaged position.

As previously described above and as shown in FIG. 9*c*, the ACL locking anchor 134*b* is coupled to a suture, which is fed into the femoral tunnel 122. The ACL 124 is then pulled up through the femoral tunnel 122 to a point that the ACL 124 reaches the locking cavity 130. Optionally, the ACL 124 is coupled to the locking cavity by the introduction of bone cement through the transverse cavity.

Figure 20:
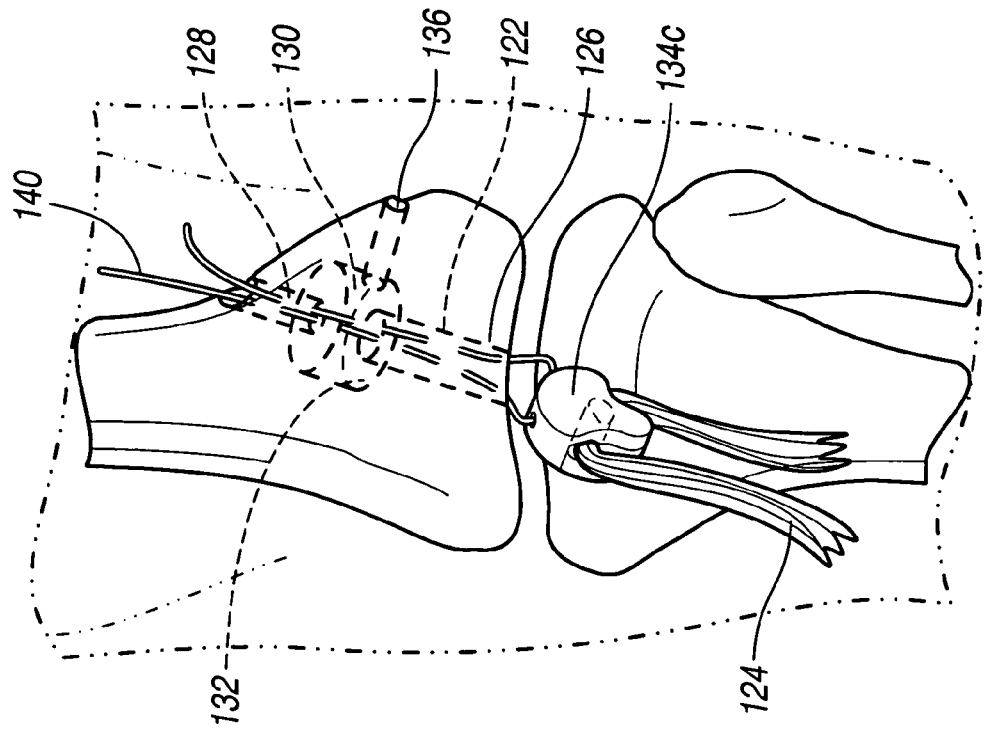
FIG. 20 represents an alternate method of coupling an ACL into a femoral tunnel.
Figure 19A:
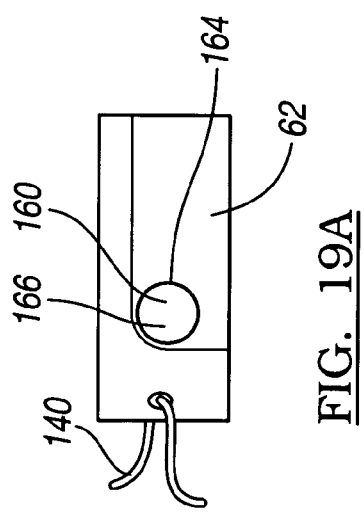
FIGS. 19a and 19b represent alternate soft tissue implants according to another embodiment of the present invention.
Figure 19B:
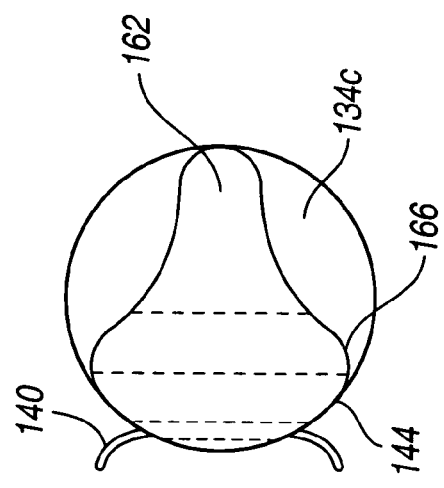

FIGS. 19, 19*b*, and 20 represent another embodiment of the invention. The ACL anchor 134*c* defines a though passage 160 which accepts an ACL 124 therethrough. Additionally shown is a saddle bearing surface 162. The through passage 160 defines a first seat 164 which bears the ACL while it is being drawn in to the femoral tunnel. The saddle bearing surface also defines a second bearing surface 166, which functions as a bearing surface when then the locking member is rotated into its engaged position.

Figure 21A:
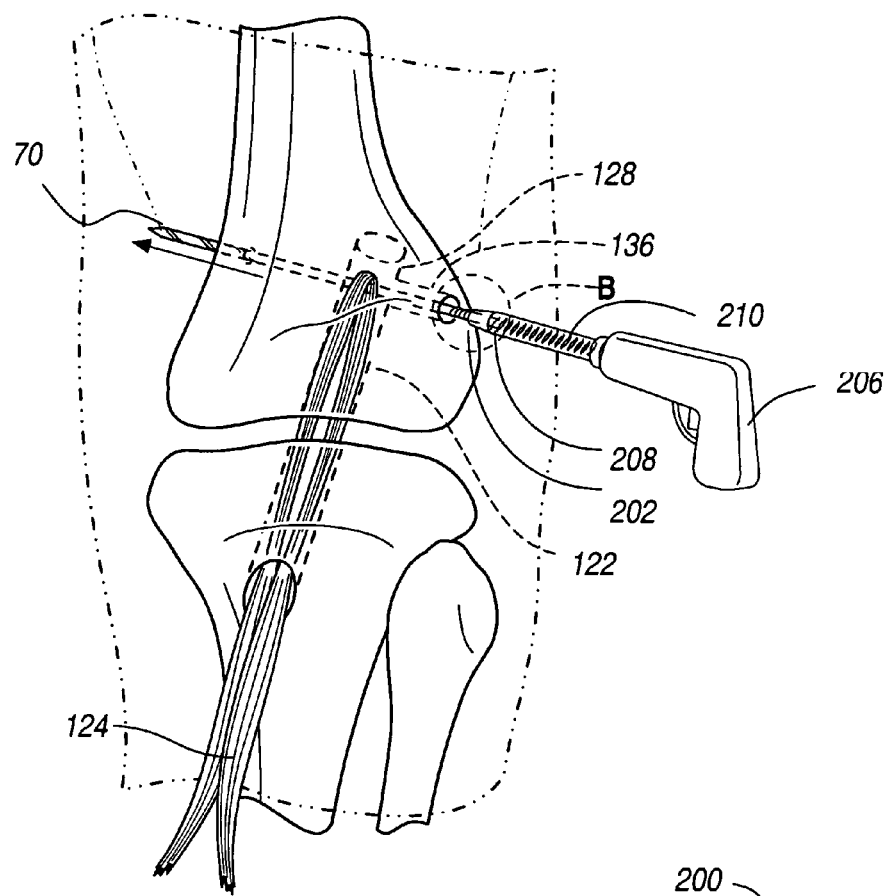
FIGS. 21a through 22 represent an alternate method of coupling an ACL into a femoral tunnel.

FIG. 21*a* represents an alternate method of coupling an ACL 124 into a femoral tunnel 128. After preparing the transverse tunnel 136 in the femur, a cross pin 70 is positioned transverse to the tunnel 136. The ACL 124 is now pulled over the cross pin 70 as previously described. The cross pin 70 has an exterior surface 200 which has a threaded portion 202. The thread 202 is configured to threadably engage a nozzle portion 204 of a glue/bone cement injection gun 206. In this regard, the nozzle portion 204 has a forward internally threaded conical portion 208 that is fluidly coupled to a polymer mixing portion 210. The nozzle portion 204 is coupled to the cement gun 206 using a threading coupling 212.

Figure 21B:
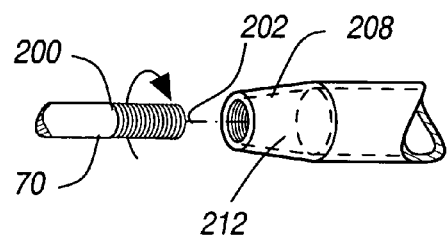
Figure 22:
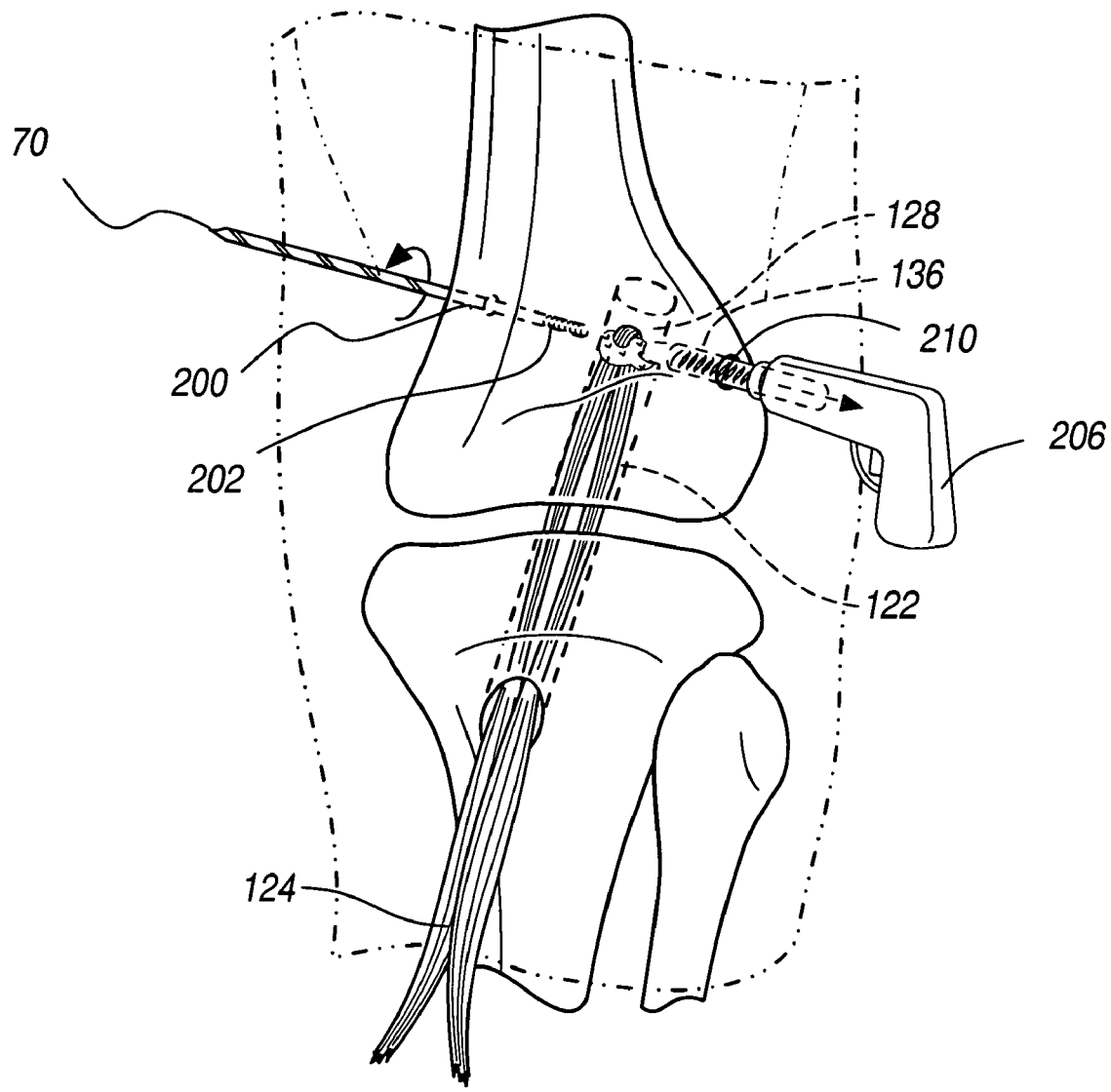

As shown in FIGS. 21*b* and 22, the cement gun 206 and corresponding nozzle portion 204 are coupled to the cross pin 70 and translated through the femur so as to cause the nozzle portion 204 to displace the cross pin 70 and support the ACL 124 within the tunnel 136. At this point, the pin 70 can be rotated to decouple the pin 70 from the nozzle portion 204.

To fixably couple the ACL 124 into the tunnel 136, a trigger of the cement gun 206 is actuated to fill the tunnel 136 with bone cement or glue. In this regard, the tunnel 136 is filled with cement or glue while the nozzle portion 204 is being retracted toward the bone cement gun 206. As previously described, the cement is allowed to set prior to fixation to the tibia.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of surgically implanting a soft tissue replacement for attaching two bone members comprising:
    forming a femoral tunnel having a first portion having a first diameter and a second portion having a second diameter which is smaller than the first diameter;
    forming a locking cavity between the first and second portions, the locking cavity configured to provide a positive locking surface;
    coupling a flexible strand to the soft tissue replacement;
    threading the flexible strand through the femoral tunnel;

pulling the flexible strand and soft tissue replacement into the locking cavity; and injecting cement into the locking cavity.

2. The method according to claim 1 further comprising forming a transverse passage and injecting cement through the transverse passage so as to substantially fill the locking cavity.

3. The method according to claim 1 further comprising forming a transverse passage which intersects the locking cavity and injecting cement through the transverse passage so as to substantially fill the locking cavity.

4. The method according to claim 3, wherein forming the transverse passage includes forming the transverse passage to intersect only one side of the locking cavity.

5. The method according to claim 1, further comprising removing the flexible strand from the soft tissue replacement and femoral tunnel before injecting cement into the locking cavity.

6. The method according to claim 1, wherein coupling a flexible strand to the soft tissue replacement includes coupling a mid-section of a flexible strand to the soft tissue replacement; and
   wherein threading the flexible strand through the femoral tunnel includes threading free ends of the flexible strand through the femoral tunnel.

7. A method of surgically implanting a soft tissue replacement for attaching two bone members comprising:
   forming a tunnel within a bone, the tunnel having a first portion with a first diameter and a second portion, the tunnel having an axis;
   forming a locking cavity within the tunnel, the locking cavity located between the first portion and the second portion of the tunnel and coaxial with the axis of the tunnel, said locking cavity being configured to provide a positive locking surface, said locking cavity having a second diameter larger than the first diameter;
   providing a locking member configured to engage the soft tissue replacement;
   threading the soft tissue through the bone tunnel; and
   engaging the locking member and soft tissue replacement with the positive locking surface in the locking cavity, wherein the locking member is wholly positioned within the looking cavity.

8. The method according to claim 7 further comprising forming the locking member by injecting a curable liquid in the locking cavity and allowing the curable liquid to cure around a portion of the soft tissue replacement.

9. The method according to claim 7 wherein providing a locking member includes providing a one-piece locking member having a cylindrical member with a first surface configured to engage the soft tissue implant when the locking member is in a first orientation and a second surface configured to engage the soft tissue implant when the locking member is in a second orientation.

10. The method of claim 7 further including injecting biological materials into the locking cavity.

11. The method according to claim 7 further including fluidly coupling a syringe to the locking cavity.

12. A method of surgically implanting a soft tissue replacement for attaching two bone members comprising:
   forming a tunnel having a first diameter within a bone;
   forming a locking cavity having a second diameter within the tunnel wherein the first and second diameters are different, said locking cavity being configured to provide a positive locking surface annularly disposed around the tunnel;
   providing a locking member having a first profile which allows insertion of the locking member through the tunnel and a second profile which allows engagement with the positive locking surface upon rotation of the locking member within the cavity;
   threading the soft tissue replacement through the tunnel; and
   engaging the locking member and soft tissue replacement in the locking cavity.

13. The method according to claim 12 further including rotating the locking member within the locking cavity.

14. The method according to claim 13 further comprising injecting a curable liquid in the locking cavity and allowing the curable liquid to cure around a portion of the soft tissue replacement.

15. The method according to claim 12, wherein the locking member includes a longitudinal axis such that in the first profile the longitudinal axis of the locking member is parallel to a longitudinal axis of the bone tunnel, and in the second profile, the longitudinal axis of the locking member is perpendicular to the longitudinal axis of the bone tunnel.

16. A method of surgically implanting a soft tissue replacement for attaching two bone members comprising:
   forming a tunnel within a bone the tunnel having a first portion with a first diameter and a second portion;
   forming a locking cavity within the tunnel, the locking cavity having a second diameter larger than the first diameter, said locking cavity being configured to provide a positive locking surface, the locking cavity being coaxial with the first portion of the tunnel define;
   providing a locking member configured to engage the soft tissue replacement, said locking member having a cylindrical member with a first surface configured to engage the soft tissue implant when the locking member is in a first orientation and a second surface configured to engage the soft tissue implant when the locking member is in a second orientation;
   threading the soft tissue through the bone tunnel;
   engaging the locking member and soft tissue replacement in the locking cavity,
   coupling a suture to the locking member and feeding the suture through the bone tunnel; and
   wherein feeding the soft tissue replacement through the bone tunnel includes pulling the locking member and soft tissue replacement into the locking cavity.

17. The method according to claim 16, wherein coupling a suture to the locking member includes coupling a suture to a suture receiving bore extending through the locking member transverse to a longitudinal axis of the locking member.

18. The method according to claim 17, further comprising injecting adhesive into the locking cavity, and wherein the locking member further comprises a through bore coaxial with the longitudinal axis, the through bore configured to receive the adhesive therethrough to facilitate retention of the locking member in the locking cavity.

19. A method of surgically implanting a soft tissue replacement for attaching two bone members comprising:
   forming a tunnel having a first diameter within a bone;
   forming a locking cavity having a second diameter within the tunnel wherein the first and second diameters are different, said locking cavity being configured to provide a positive locking surface;
   providing a locking member having a first profile which allows insertion of the locking member through the tunnel and a second profile which allows engagement with the positive locking surface upon rotation of the locking member within the cavity;

threading the soft tissue replacement through the femoral tunnel;

engaging the locking member and soft tissue replacement in the locking cavity;

rotating the locking member within the locking cavity;

infecting a curable liquid in the locking cavity and allowing the curable liquid to cure around a portion of the soft tissue replacement;

providing a transverse tunnel intersecting the locking cavity;

wherein the locking member further comprises a through bore coaxial with a longitudinal axis thereof, the locking member through bore being in fluid communication with the transverse tunnel; and wherein injecting a curable liquid in the locking cavity includes injecting a curable liquid through the transverse tunnel into the locking cavity such that the curable liquid flows into the through bore to facilitate engagement of the locking member in the locking cavity.

20. The method according to claim 19, wherein the transverse tunnel intersects and extends beyond the locking cavity.

21. A method of surgically implanting a soft tissue replacement for attaching two bone members comprising:

forming a tunnel having a first portion with a first diameter and a second portion in a bone;

forming a locking cavity in the tunnel, the locking cavity located between the first portion and the second portion of the tunnel and coaxial with the tunnel, the locking cavity having a second diameter larger than the first diameter, said locking cavity defining an engageable locking surface;

coupling the soft tissue replacement to a securing element so as to position the soft tissue replacement in direct contact with the securing element;

positioning the securing element with the soft tissue replacement secured thereto into the bone tunnel, said securing element being positioned wholly within the locking cavity and engaged with the locking surface;

injecting adhesive into the bone tunnel to adhesively secure the securing element to the bone tunnel.

22. The method according to claim 21, wherein the securing element comprises a first portion configured to receivably couple the soft tissue replacement thereto, and a second portion configured to engage the bone tunnel.

23. The method according to claim 21, further comprising forming a transverse passage which intersects the bone tunnel and injecting adhesive through the transverse passage such that the adhesive engages the bone tunnel and the securing element to adhesively secure the securing element to the bone tunnel.

24. The method according to claim 23, wherein forming the transverse passage includes forming the transverse passage to have a smaller diameter than the bone tunnel.

25. The method according to claim 23, wherein forming the transverse passage includes forming the transverse passage to extend through only one side of the bone tunnel.

26. The method according to claim 21 wherein forming a tunnel in a bone includes forming a tunnel through a bone having a first portion with a first diameter and a second portion with a second diameter smaller than the first diameter, the first portion having an entrance opening and the second portion having an exit opening.

27. The method according to claim 26, further comprising:
coupling a flexible strand to an aperture in the securing element; and threading the flexible strand through the bone tunnel such that the flexible strand extends beyond the exit opening;

wherein positioning the securing element with the soft tissue replacement secured thereto into the bone tunnel includes pulling the flexible strand to position the securing element and soft tissue replacement in the bone tunnel.

28. The method according to claim 27, wherein coupling a flexible strand to the securing element includes coupling a midsection of a flexible strand to the securing element; and wherein pulling the flexible strand to position the securing element and soft tissue replacement in the bone tunnel includes pulling the securing element and soft tissue replacement in the bone tunnel.

29. The method according to claim 28, wherein pulling the flexible strand includes drawing the suture up through the femoral tunnel.

30. A method of surgically implanting a soft tissue replacement for attaching two bone members comprising:

forming a tunnel in a bone;

forming a locking cavity in the bone tunnel;

coupling the soft tissue replacement to a securing element;

positioning the securing element with the soft tissue replacement secured thereto into the bone tunnel such that the securing element is positioned in the locking cavity; and injecting adhesive into the bone tunnel to adhesively secure the securing element in the locking cavity.

31. A method of surgically implanting a soft tissue replacement for attaching two bone members comprising:

forming a femoral tunnel having a first portion with a first diameter, and a second portion with a second diameter smaller than the first diameter;

forming a locking cavity between the first and second portions of the femoral tunnel, the locking cavity having a third diameter larger than the first diameter, said locking cavity located between the first portion and the second portion of the femoral tunnel and co-axial with the femoral tunnel and configured to provide a positive locking surface;

forming a transverse tunnel intersecting the locking cavity;

providing a locking member having a first profile which allows insertion of the locking member through the femoral tunnel and a second profile which allows engagement with the positive locking surface upon rotation of the locking member within the locking cavity, the locking member including a longitudinal axis, a through bore parallel to the longitudinal axis and a transverse bore adjacent one end of the locking member;

coupling a suture to the transverse bore;

threading the suture through the femoral tunnel;

coupling the soft tissue replacement to a recessed area of the locking member;

pulling the locking member and soft tissue replacement through the femoral tunnel into the locking cavity;

engaging the locking member and soft tissue replacement in the locking cavity; and injecting adhesive through the transverse tunnel into the locking cavity such that the adhesive substantially fills the locking cavity and surrounds the locking member.

32. The method according to claim 31, wherein engaging the locking member and soft tissue replacement in the locking cavity includes rotating the locking member in the locking cavity such that the longitudinal axis of the locking member is substantially perpendicular to a longitudinal axis of the femoral tunnel.

33. The method according to claim 32, wherein the transverse tunnel intersects and extends beyond the locking cavity; and wherein the injected adhesive flows through the through bore of the locking member and into a portion of the transverse tunnel that extends beyond the locking cavity to facilitate securing the locking member to the locking cavity.

\* \* \* \* \*

UNITED STATES PATENT AND TRADEMARK OFFICE
CERTIFICATE OF CORRECTION

PATENT NO.      : 7,896,917 B2
APPLICATION NO. : 11/201491
DATED           : March 1, 2011
INVENTOR(S)     : Troy M. Walters et al.

Page 1 of 1

It is certified that error appears in the above-identified patent and that said Letters Patent is hereby corrected as shown below:

Column 3, line 13, delete "and"

Column 3, line 20, "accordance" should be -- according --

Column 3, line 20, insert -- of -- after "embodiment"

Column 8, line 7, insert -- be -- after "may"

Column 10, line 17, "FIGS. 19" should be -- FIGS. 19A --

Column 10, line 18, "though" should be -- through --

Column 11, line 44, "looking" should be -- locking --

Column 12, line 32, delete "define"

Column 13, line 8, "infecting" should be -- injecting --

Signed and Sealed this
Thirty-first Day of July, 2012

David J. Kappos
*Director of the United States Patent and Trademark Office*